(12) United States Patent
Tennican

(10) Patent No.: US 11,160,919 B2
(45) Date of Patent: Nov. 2, 2021

(54) MIXING/ADMINISTRATION SYSTEM FOR VACCINES AND MEDICAMENTS

(71) Applicant: Hyprotek, Inc., Spokane, WA (US)

(72) Inventor: Patrick O. Tennican, Spokane, WA (US)

(73) Assignee: Hyprotek, Inc., Spokane, WA (US)

(*) Notice: Subject to any disclaimer, the term of this patent is extended or adjusted under 35 U.S.C. 154(b) by 0 days.

(21) Appl. No.: 17/259,132

(22) PCT Filed: Jul. 9, 2019

(86) PCT No.: PCT/US2019/041076
§ 371 (c)(1),
(2) Date: Jan. 8, 2021

(87) PCT Pub. No.: WO2020/014278
PCT Pub. Date: Jan. 16, 2020

(65) Prior Publication Data
US 2021/0154391 A1    May 27, 2021

Related U.S. Application Data

(60) Provisional application No. 62/695,800, filed on Jul. 9, 2018.

(51) Int. Cl.
| | |
|---|---|
| G06K 19/07 | (2006.01) |
| A61J 1/20 | (2006.01) |
| A61M 5/00 | (2006.01) |
| G16H 20/17 | (2018.01) |
| A61M 5/19 | (2006.01) |

(Continued)

(52) U.S. Cl.
CPC ............ *A61M 5/002* (2013.01); *A61J 1/2037* (2015.05); *A61J 1/2096* (2013.01); *A61M 5/19* (2013.01);
(Continued)

(58) Field of Classification Search
CPC ............... A61M 5/002; A61M 5/19; A61M 2205/502; A61M 2205/52;
(Continued)

(56) References Cited

U.S. PATENT DOCUMENTS

| | | | |
|---|---|---|---|
| 9,082,157 B2 * | 7/2015 | Gibson | G06Q 10/08 |
| 10,076,609 B2 * | 9/2018 | Ashby | A61M 5/31513 |

(Continued)

OTHER PUBLICATIONS

Invitiation to Pay Addition Fees dtd Oct. 1, 2019 for PCT Application No. PCT/US2019/041076, "Mixing/Administration System for Vaccines and Medicaments", 14 pages.
(Continued)

*Primary Examiner* — Michael G Lee
*Assistant Examiner* — David Tardif
(74) *Attorney, Agent, or Firm* — Lee & Hayes, P.C.

(57) ABSTRACT

Mixing/administration systems and methods for preparing an agent for administration to an individual are disclosed. Caps may be included as part of the system, which may include compositions comprising at least one of a cleansing, antiseptic, antimicrobial, or disinfectant agent. The caps may additionally be included that may be used for hemostasis at an injection site. Packaging and/or the mixing/administration system within it may include a tracking mechanism for data tracking regarding many different aspects of the system, including aspects of manufacture and administration.

18 Claims, 8 Drawing Sheets

(51) Int. Cl.
*G06K 19/06* (2006.01)
*G06Q 30/00* (2012.01)

(52) U.S. Cl.
CPC .......... *G06K 19/06028* (2013.01); *G06K 19/06037* (2013.01); *G06K 19/0723* (2013.01); *G06Q 30/018* (2013.01); *G16H 20/17* (2018.01); *A61M 2205/502* (2013.01); *A61M 2205/52* (2013.01); *A61M 2205/6054* (2013.01); *A61M 2205/6072* (2013.01)

(58) Field of Classification Search
CPC .... A61M 2205/6054; A61M 2205/6072; A61J 1/2037; A61J 1/2096; G16H 20/17; G06K 19/06028; G06K 19/06037; G06K 19/0723; G06Q 30/018
USPC .......................................................... 700/2
See application file for complete search history.

(56) References Cited

U.S. PATENT DOCUMENTS

| | | | |
|---|---|---|---|
| 10,307,548 B1* | 6/2019 | Hunt | A61M 5/5086 |
| 2006/0079834 A1 | 4/2006 | Tennican et al. | |
| 2009/0093757 A1 | 4/2009 | Tennican | |
| 2013/0345626 A1 | 12/2013 | Tennican | |
| 2017/0232204 A1* | 8/2017 | Knapp | A61M 5/28 604/66 |
| 2018/0221564 A1* | 8/2018 | Patel | A61L 2/081 |
| 2019/0217018 A1* | 7/2019 | Bauss | A61M 5/3213 |

OTHER PUBLICATIONS

The PCT Search Rpeort and Written Opinion dated Dec. 4, 2019, for PCT Application No. PCT/US2019/041076, 17 pages.

\* cited by examiner

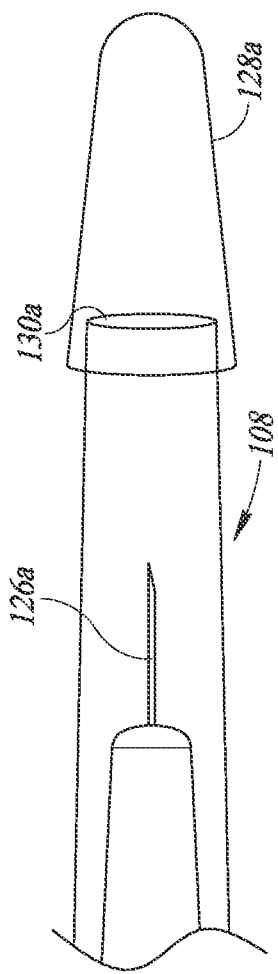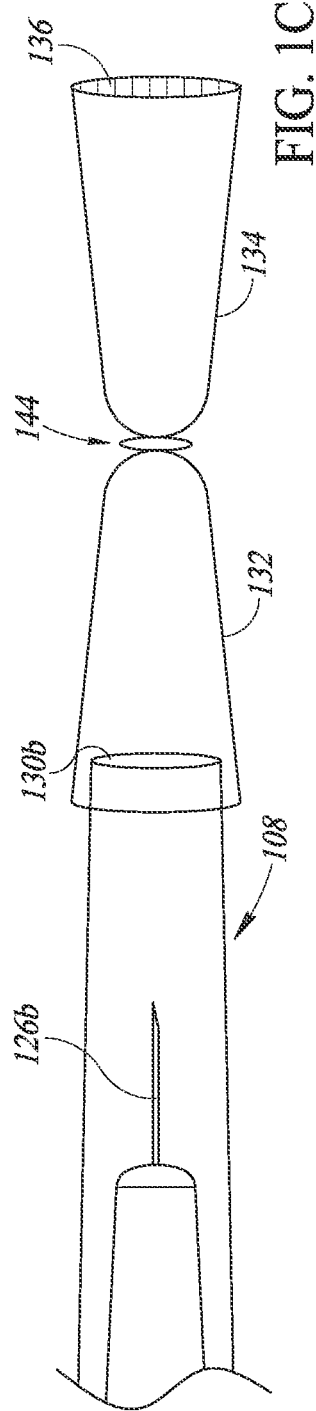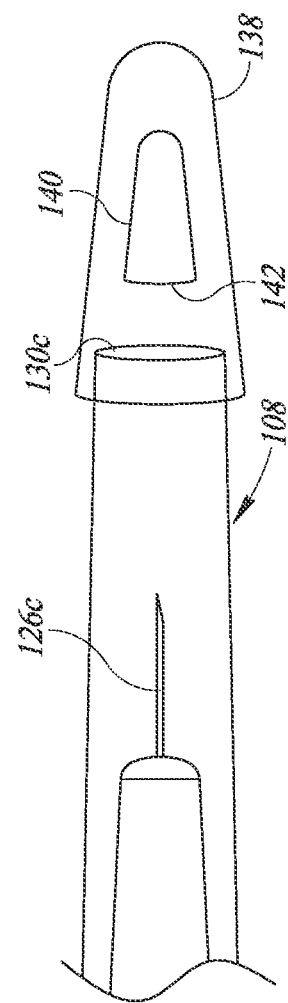

MIXING/ADMINISTRATION SYSTEM FOR VACCINES AND MEDICAMENTS

CROSS-REFERENCE TO RELATED APPLICATIONS

This application claims priority to and is a National Phase of International Application No. PCT/US19/41076, filed Jul. 9, 2019, which claims priority to U.S. Provisional Patent Application No. 62/695,800, filed Jul. 9, 2018, titled "Mixing/Administration System for Vaccines and Medicaments," the entire contents of which are incorporated herein by reference.

BACKGROUND

Conventionally, a provider administering an injection must first locate, gather, and/or assemble an antiseptic agent and an applicator (e.g., cotton ball) to cleanse the skin at the site of an injection and/or to disinfect the needle used for the injection. This preliminary step may be inconvenient and may risk error or contamination of the needle as the provider gathers the antiseptic and/or disinfecting supplies.

Moreover, conventionally, after administering an injection, a provider must separately locate an object that can be used to apply pressure and/or a hemostatic agent to an injection site to stop bleeding at the injection site.

Additionally, it has traditionally been difficult to track data regarding particular injections, especially in third-world countries. Being able to track the specific patient who receives a specific injection from a specific vial, syringe, and/or package could have benefits for epidemiology (for example, stopping epidemics of infectious disease such as measles or rubella), thoroughness of medical records, and/or stopping the administration of ineffective, heat-inactivated, and/or contaminated lots of medicaments.

A variety of other problems may occur when utilizing conventional methodology and devices for mixing and/or administering medicaments to an individual. For example, where multiple components are to be mixed, extraction and transfer of one component and introduction of such component into another component may potentially expose one or both of the components to a non-sterile or contaminated environment leading to contamination of the resulting medicament. Additionally, incomplete extraction or improper measurement of one or more components may result in preparation and/or administration of an improper dosage. In particular instances, once a medicament is mixed, the mixture must again be extracted from a vial or container into a syringe prior to administering to an individual. Such additional transfer may lead to additional opportunities for contamination, incomplete extraction of contents, and/or inaccurate measuring of a component or the resulting medicament.

In practice, there is limited availability of sterile environments for maintaining sterility during transfer and/or mixing of components, or preparation and transfer of medicaments. Additional errors may result from use of the wrong diluent to reconstitute the vaccine. Preparation of medicaments utilizing multiple components may be tedious and time consuming due to factors such as the need to access individually packaged items such as separate vials and/or transfer devices, or to measure one or more components to be combined to form the medicament.

Healthcare acquired infection (HAI) has been recognized as a significant cause of preventable mortality and morbidity. In the United States, HAI annually costs nearly 99,000 lives and billions of dollars in additional treatment and hospitalization. Klevens, et al., *Estimating Health Care-Associated Infection and Deaths in U.S. Hospitals,* 2002, Public Health Reports, Vol. 122, p. 160, 2007. Contamination of intravascular catheters, surgical sites, and invasive procedure sites, frequently leads to device removal and replacement, prolonged parenteral antimicrobial therapy, and extended hospitalizations and rehabilitation.

Multi-antimicrobial resistant organisms frequently are spread by healthcare providers' hands or medical equipment, from one colonized or infected patient to other susceptible patients. Surgical and injection site infections may result from inadequate antiseptic preparations of the skin. Widespread use of chlorhexidine gluconate (CHG) for routine washing and wiping of pre-operative sites, has led to the increased incidence of resistant *Staphylococcus aureus,* both to methicillin (MRSA) and CHG, in some hospital environments.

Another factor to be considered when preparing medicaments for administration is the nature of the medicaments contained in the device and/or device components. For example, agents contained within device components may be potentially harmful to handlers upon exposure. Such potentially harmful agents include but are not limited to allergens, teratogens, endocrine-disruptors, carcinogens, or otherwise toxic or potentially toxic materials. Many conventional medicament administration devices potentially expose the handler of such device to the medicaments being administered or prepared during the preparation and administration processes.

SUMMARY

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter.

This disclosure describes sterile mixing-administration systems for vaccines, antimicrobials, and immunotherapy.

In embodiments, a mixing-administration system can include a dual-chamber syringe device, one or more caps that can be used before or after the injection (e.g., to apply a disinfecting, antimicrobial, cleansing, antiseptic, and/or hemostatic agent, to apply pressure to an injection site, etc.), packaging, and methods of mixing and administration of medicaments using the device. In embodiments, the mixing-administration system can include a tracking mechanism included on packaging for a syringe or on a vial, wherein the syringe may include a medicament, and systems and methods of using a tracking mechanism.

In embodiments, the mixing-administration system can include packaging, a tracking mechanism, and any syringe. In embodiments, the syringe can include a medicament associated with the tracking mechanism. In embodiments, the mixing-administration systems can include a method of tracking manufacture and administration of vaccines with the syringes.

In embodiments, the tracking mechanism can be used for collection and analysis of individual and aggregate data related to vaccination. In embodiments, the tracking mechanism can be scanned and associated with manufacturing data about the medicament or syringe. In embodiments, at or around the time of injection, the tracking mechanism may be scanned by a smartphone, handheld scanner, etc., and associated with data regarding the administration of the vaccine.

By the association of the administration data with the manufacturing data via the tracking mechanism, information can be provided regarding when, where, and to whom particular vaccines were administered, allowing strategic remediation of outbreaks, among other uses.

In embodiments, the tracking mechanism can be included on a label that also comprises a viability indicator. The viability indicator can provide a visual cue (e.g., a color change) if the package deviates from a certain temperature range or is exposed to certain types or degrees of light. In embodiments, a viability indicator may be included as a separate label to packaging or on a vial.

In accordance with example implementations, embodiments of mixing/administration systems are provided that may include a dual-chamber syringe device (that can include a medicament vial; a syringe assembly comprising a barrel and a piston; a protective material supporting the syringe assembly and medicament vial; a member within the system, the member separating the piston of the syringe assembly from the vial), one or more caps for application of pressure and/or one or more agents for disinfection, antimicrobial effect, and/or hemostasis; and packaging. In examples, the packaging may include a tracking mechanism (e.g., barcode, RFID tag, etc.)

In embodiments, the dual-chamber syringe device includes a chamber containing a medicament in a vial, and an internal chamber within a syringe barrel that contains a diluent. In embodiments, a fluid passageway extends through a syringe piston insertable into a back end of the internal chamber. A valve is associated with the passageway controlling fluid passage through the syringe piston.

In embodiments, the dual-chamber syringe device includes a vial penetrator having a head segment and a body portion, with a channel through the body portion and through at least one surface of the head without passing through the tip. In embodiments, the dual-chamber syringe device includes a stem extending from the back end to a vial housing. The vial housing extends to the external portion of the syringe piston and is configured to house a container (e.g., a vial). A fluid passageway extends from the vial housing through the piston stem and through the first end of the piston.

In embodiments, the disclosure encompasses methods of preparing a medicament for administration to an individual using the dual-chamber syringe device. A first component (e.g., a vaccine powder, etc.) is provided within a medicament vial and a second component (e.g., a diluent, etc.) is provided within a syringe barrel chamber. A closed valve is associated with a fluid passageway between the medicament vial and the syringe barrel through a piston. Valve repositioning allows fluid passage and sliding of the piston joins the first and second components. Repeated sliding of the piston mixes the components to produce the medicament.

As used herein, a "medicament" is a medicine, medication, or drug that has an immunogenic response in an amount effective for a desired outcome in preventing, curing, or treating disease. In embodiments, a medicament may be for any purpose including antiviral, antimicrobial, antibacterial, etc. In embodiments, the medicament can include, but is not limited to, measles-rubella (MR) and measles-mumps-rubella (MMR). As used herein, a "vaccine" may refer to lyophilized vaccine, or a vaccine reconstituted with a liquid diluent. In embodiments, a vaccine can be live-attenuated, inactivated, subunit, toxoid, subunit, recombinant, polysaccharide, and/or conjugate. As used herein, a "vaccine" may refer to the medicament being administered in the vaccine.

In embodiments, a dual-chamber syringe device includes a vial integrated into a plunger base that may be rotated such that a channel is opened and later, after mixing, it may be rotated again to close the channel. The vial is opened such that the vaccine may be diluted. Vial housing may be different or non-existent in this embodiment. In embodiments, a window or shutter indicates placement of the vial.

In embodiments, the mixing/administration system includes packaging. In embodiments, the packaging can encase a syringe (e.g., a dual-chamber syringe or any syringe). In embodiments, the packaging comprises a protective film. In embodiments, the protective film is loose or "active" to allow manipulation of the system components relative to one another without opening or puncturing the protective film. In embodiments, a mixing/administration system or components of a mixing/administration system can be sterilized by methods that are safe for the particular vaccine.

In an aspect, the protective film includes at least one of polypropylene (PP), polyvinyls, aluminum foil, aluminum oxide coated nylon, biaxially oriented (biax) nylon (BO nylon), biax polyethylene terephthalate (BOPET), aluminum oxide coated BOPET, polycarbonate, oriented polypropylene (OPP), biax OPP (BOPP), high density polyethylene (HDPE), medium density polyethylene (MDPE), low density polyethylene (LDPE), linear low density polyethylene (LLDPE), ethylene vinyl acetate copolymer (EVA), metallocene, ionomer, polyvinylidene chloride (PVdC), metallized PET, metallized OPP, poly(ethylene vinyl alcohol) (EVOH), coex, surlyn, silicon oxide coated BOPET, or paper. In embodiments, the protective film may be formed to at least partially conform to the shape of contents of the protective film. In embodiments, the protective film may be heat sealed to at least some of the contents of the protective film.

In embodiments, the mixing/administration system includes a tracking mechanism (e.g., linear barcode, matrix barcode, RFID tag, etc.). Data regarding administration of a vaccine that includes the medicament encased in the packaging to which the tracking mechanism is attached, and data regarding manufacture and/or contents of the medicament, can be stored in association with a tracking mechanism identifier, and so in association with each other.

In embodiments, the tracking mechanism may be affixed to the packaging or may be affixed to a label affixed to the packaging. In embodiments, a tracking mechanism may be affixed to a vial included in a syringe inside in the packaging. In embodiments, both the packaging and a vial of a syringe can include one or more tracking mechanisms with the same or different tracking mechanism identifiers.

In embodiments, the tracking mechanism (e.g., barcode) may be created, imported by an application executing on a user device, or scanned by a smartphone, handheld scanner, etc., and stored in a data record that includes or is associated with data regarding the manufacture of the medicament, diluent, vial, or other components of the mixing/administration system or other syringe system.

As used herein, "user device" may refer to one or more of a specialized device, a consumer device, a smartphone, a tablet, a secured device, a satellite communication device, etc.

In embodiments, at or around the time of injection of the medicament, the tracking mechanism (e.g., barcode) may be scanned by a smartphone, handheld scanner, etc., and stored in a data record that also contains data regarding the administration of the injection.

As used herein, a "barcode" may refer to a linear (one-dimensional) barcode, or a matrix barcode (alternatively referred to as a two-dimensional barcode or 2D code). Examples of linear barcodes include but are not limited to Code 25, Code 39, Code 128, EAN-8, EAN-13, UPC-A, and UPC-E. Examples of matrix barcodes include but are not limited to Aztec Code, Code 1, d-touch, Data Matrix, DotCode, High Capacity Color Barcode, MaxiCode, PDF417, and QR code.

Alternatively or additionally to containing a barcode, a radio frequency identification (RFID) tag may be attached to or contained in the packaging.

As noted above, in embodiments, an appropriate tracking mechanism may be useful for identifying and tracking lots, for record keeping purposes regarding the medicaments, and/or for patient-specific information. Such tracking may provide an additional safety measure in a vaccination effort. For example, in the event of an adverse reaction upon administering a prepared medicament, information provided via a barcode or RFID tag may be utilized to identify source, lot number, etc., which may in turn be utilized to track other vials, syringes, packages, etc., containing medicament from the identified lot. Such tracking may additionally be utilized to identify other people who may be at risk. Additionally, tracking may provide information regarding a particular reaction, etc. In the event of adverse reaction or identification of defect, analysis of any material retained within the device after administration may be analyzed by, for example, analysis techniques including but not limited to mass spectrometry and/or gas-liquid chromatography. Appropriate reporting to the FDA or other government or non-government entities may then be performed.

The manufacturing data and administration data can be stored and analyzed in association with each other, via both data's association with the tracking mechanism. Reports and/or queries may be run from the manufacturing data and/or the administration data associated with the tracking mechanism for any number of purposes, such as for tracking who received what was later determined to be a compromised batch of medicament, determining a percentage of a population in a geolocation that has received a particular vaccine, etc.

In embodiments, the servers to which the administration data and manufacturing are sent can be associated with any of a government agency, a manufacturer of the medicament or syringe, a health organization, etc. In embodiments, information (e.g., search results, query results, reports, filtered data) from the servers can be sent to a government agency (e.g., Centers for Disease Control (CDA), Food and Drug Administration (FDA), etc.), a manufacturer of the medicament or syringe, a health organization (e.g., World Health Organization (WHO), etc.), etc.

In embodiments, a viability indicator can be included as part of the tracking mechanism, on the tracking mechanism, or included elsewhere on or inside the packaging. In embodiments, the viability indicator comprises a label. The viability indicator can indicate a level of heat and/or light exposure that could affect the effectiveness of a vaccine. The viability indicator can be visually or digitally scanned simultaneously or sequentially with scanning the tracking mechanism.

The mixing/administration systems described herein may include one or more caps on a syringe device. In embodiments, one or more caps are detachably connected to the needle end of the syringe barrel. Multiple caps may be attached together in succession with each other. In embodiments, one or more caps are detachably connected to a needle protector wherein the needle protector is detachably connected to the needle end of the syringe barrel and covers a needle. In embodiments, one cap may be removably contained in another cap.

In embodiments, at least one cap may contain a composition comprising one or more cleansing, antiseptic, antimicrobial, or disinfectant agents. In embodiments, at least one cap may contain one or more hemostatic agents. In embodiments, at least one cap may contain a composition comprising a combination of one or more hemostatic agents and one or more cleansing, antiseptic, antimicrobial, or disinfectant agents. In embodiments, at least one cap may contain a dry applicator material without a cleansing, antiseptic, antimicrobial, disinfectant, or hemostatic agent, which, in examples, may be utilized for pressure on an injection site.

In embodiments, at least one cap may include a removable protective lid affixed to the rim of the cap that seals the cap. The removable protective lid, while it is in place over the cavity of the cap, may prevent a cap contained within the cap (and other contents such as an applicator material and/or antimicrobial composition) from escaping. In embodiments, the removable protective lid may be sealed around a periphery of the cavity by, for example, an adhesive (e.g., silicone, silicone rubber, synthetic resin, methyl methacrylate, for example), a thermoplastic, sonic welding, microwave welding, thermal bonding, induction heating, or the like. In embodiments, the protective film may be a gas/liquid impermeable, pore-free (i.e., thicker than 1 micron), flexible material such as aluminum oxide, silicon oxide, or the like.

In embodiments, at least one cap may contain an applicator material (e.g., polymeric sponge) with which to apply the composition(s) or with which to apply pressure to an injection site. In embodiments, at least one cap may contain an applicator material that is compressed and that expands above the rim of the cap when the removable protective lid on the rim is broken or removed. In embodiments, at least one cap may contain an applicator material that expands above the rim of the cap when the cap is detached from another component of the mixing/administration system (e.g., detached from the syringe barrel, detached from the packaging, detached from another cap, etc.) and an end of the cap is exposed.

Additionally or alternatively, in embodiments, at least one cap may be designed to provide a sanitized surface with which to apply pressure at an injection site should an individual start bleeding at the injection site. In embodiments, applicator material contained in the at least one cap can be pressed against the injection site to apply pressure.

In embodiments, a needle protector may include applicator material and/or cleansing, antiseptic, antimicrobial, disinfectant, or hemostatic agents as described above and below.

In embodiments, at least one cap can be enclosed in the packaging separate from the syringe device. In embodiments, at least one cap can be packaged in a recess of the packaging separate from the syringe device.

BRIEF DESCRIPTION OF THE DRAWINGS

The detailed description that follows is described with reference to non-limiting and non-exhaustive embodiments shown in the accompanying figures. In the figures, the left-most digit(s) of a reference number identifies the figure in which the reference number first appears. The same reference numbers in different figures indicate similar or identical items.

FIG. 1B is a side view of an example of a needle end of a mixing/administration system that includes a cap, in accordance with an aspect of the disclosure.

FIG. 1C is a side view of an example of a needle end of a mixing/administration system includes a first cap removably attached to a second cap, in accordance with an aspect of the disclosure.

FIG. 1D is a side view of an example of a needle end of a mixing/administration system that includes a second cap contained inside of a first cap, in accordance with an aspect of the disclosure.

DETAILED DESCRIPTION

Overview

The following description sets forth specific exemplary embodiments of systems and methods of use of the systems that incorporate elements recited in the appended claims. The embodiments are described with specificity in order to meet statutory requirements. However, the description itself is not intended to limit the scope of this patent application. Rather, the inventors have contemplated that the claimed disclosure might also be embodied in other ways, to include different elements or combinations of elements similar to the ones described in this document, in conjunction with other present or future technologies.

It would be desirable to develop alternative methodology and systems for preparation and administration of medicaments to include one or more cleansing, antiseptic, antimicrobial, disinfectant, or hemostatic agents in the packaging of a syringe device or on a vial included in a syringe device.

It would be desirable to develop alternative methodology and systems for preparation and administration of medicaments to include a sterile surface or hemostatic agent in the packaging of a syringe device or on a vial included in the syringe device that could be used to stop bleeding at an injection site.

It would be desirable to develop alternative methodology and systems for preparation and administration of medicaments to include a tracking mechanism to track information about the administration of individual vaccines.

In general aspects, the disclosure pertains to simple, safe, trackable, sterile, efficient, and effective vaccine and medicament delivery, including in resource limited environments. In addition, the disclosure pertains to systems utilized for mixing and/or administering medicaments. Devices, components of devices, packaging, and methods of mixing and/or administration are encompassed by the disclosure and are depicted and described herein.

Embodiments of the disclosure provide simple, safe, trackable, sterile, efficient, and effective vaccine and medicament delivery, including in resource limited environments.

It is to be understood that many of the concepts of the present disclosure may be utilized in conjunction with, or may be adapted to, other device configurations including conventional syringe devices and components, and those yet to be developed.

Syringe devices, other devices, packaging, and tracking mechanisms of the disclosure are not limited to particular sizes and may vary (e.g., depending upon the volume of vaccine to be mixed and/or administered, manufacturing process, etc.). Accordingly, it is to be understood that the accompanying drawings are for illustrative purposes only and are not meant to limit the syringe device, other devices, packaging, tracking mechanisms, or any other component of a mixing/administration system to any particular size or volumes.

Figure 1A:
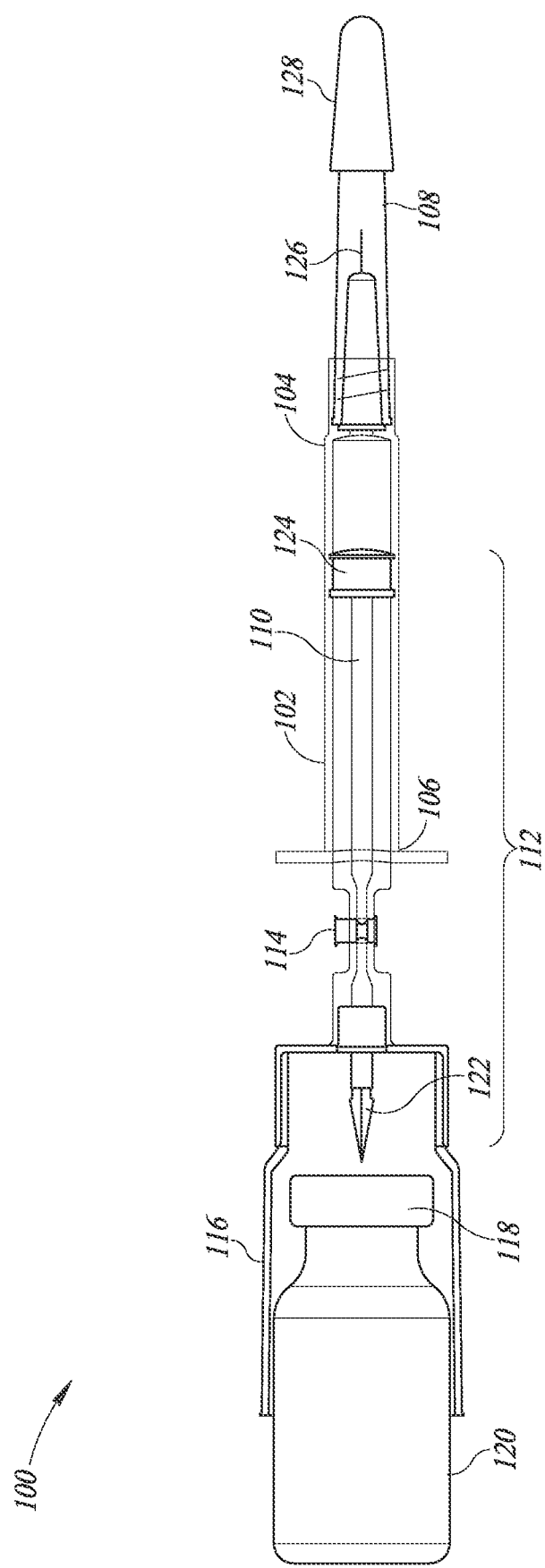
FIG. 1A is a side view of an example of a mixing/administration system, in accordance with an aspect of the disclosure.

FIG. 1A illustrates a side view of an example of a mixing/administration system in accordance with an aspect of the disclosure. Mixing/administration system 100 includes a syringe barrel 102 having a first end 104 and an opposing second end 106. First end 104 may be configured to reversibly attach to a needle 126 or other medical equipment. Such reversible attachment may be, for example, a twist-type fitting such as a LUER-LOK® fitting, or an alternative type fitting. Needle protector 108 may be provided to cover an opening at first end 104 or to cover needle 126 disposed at first end 104. Syringe barrel 102 may be described as having internal chamber 110. In embodiments, one or more caps 128 are removably attached to the distal end of needle protector 108. In embodiments, the mixing-administration system 100 may include at least one port (not shown) connecting to at least one infusion bag (not shown).

In embodiments, mixing/administration system 100 further includes a piston 112 that is insertable into internal chamber 110 of syringe barrel 102 through second end 106 as depicted in FIG. 1. In the configuration shown, piston 112 includes valve 114 and includes vial housing 116 having opening 118 and housing a container such as vial 120 (which may be referred to as a medicament vial herein) as illustrated. It is noted that vial housing 116 partially encases vial 120 providing a compartment with opening 118. Vial penetrator 122 may have a base portion, a head portion having a tip, and a stem portion extending between the base and the head, which may resemble an arrowhead shape. A fluid passageway (not shown) runs longitudinally centrally through the base portion and the stem and emerges from a side of the head portion of the vial penetrator 122 at a location other than tip. This configuration allows puncture of a septum to occur without coring. The shape of the vial penetrator 122 allows the septum to be retained across the stem portion and assists in retaining the vial 120 from pulling back off the syringe after piercing has occurred. In another embodiment, vial penetrator 122 may have a circular tip rather than a pointed tip, which may also pierce the septum without coring. In embodiments, after penetration, vial penetrator 122 permanently disables the mixing/administration system 100 and prevents reuse of either syringe barrel 102 or vial 120.

In embodiments, vial 120, protected by the vial housing 116, comprises a clean chamber for a vaccine and additives required to preserve viability and prevent bacterial contamination. When vial 120 inside the sterile packaging is engaged by a vial penetrator, the sterility of mixing-administration is ensured, up to subcutaneous delivery by a sterile needle through sanitized skin.

In embodiments, the mixing/administration system 100 may also have a variable size syringe barrel, variable diluent volume, and/or a variable size vial housing 116 for a variable size vial. In an example, the mixing/administration system is configured to deliver about 3 cc to about 60 cc, or about 0.25 to about 2.99 cc, or about 0.05 to about 0.25 cc.

In embodiments, mixing/administration system 100 may be provided in an initial "pre-mixed" condition. In embodiments, a diluent is provided within internal chamber 110 and a medicament component is provided in vial 120 within vial housing 116. In its initial state, mixing/administration system 100 is provided to have a portion of syringe piston 112 including piston seal 124 inserted within syringe barrel 102. In this initial configuration vial 120 is positioned against the back of vial housing 116.

When mixing is desired, vial 120 may be manipulated via access through opening in vial housing 116 and may be slid forward to bring vial 120 into contact with vial penetrator 122 and, using sufficient force, may allow piercing of a septum of vial 120 by vial penetrator 122 to establish fluid communication between the fluid passageway (not shown) through vial penetrator 122 and vial 120. Once vial penetrator 122 is engaged across the septum, the shape of vial penetrator 122 along with the textured internal sidewalls assists in maintaining the positioning of vial 120 in the forward position within vial housing 116.

Once fluid communication has been established between vial 120 and fluid passageway (not shown), valve 114 may be repositioned to an "on" position to allow fluid communication between vial 120 and syringe barrel 102. Piston 112 may then be slid forward into syringe barrel 102 to cause fluid transfer between internal chamber 110 and vial 120. Repeated forward and backward sliding motion of the piston may be utilized to mix the components to produce a liquid vaccine formulation. Such mixing may be further assisted by, for example, shaking, agitating, and/or swirling of mixing/administration system 100.

When sufficient mixing has occurred, the mixed medicament may be drawn into internal chamber 110 by withdrawing syringe piston 112 to its original position. Valve 114 is then repositioned to the "closed" position to block fluid communication between internal chamber 110 and vial housing 116. When administration is desired, needle protector 108 and cap(s) 128 may be removed to expose needle 126 or appropriate attachment fitting for injection by needle, IV port, etc.

Needle 126 may be attached to syringe barrel 102 as packaged, in embodiments, covered by removable needle protector(s) 108. In embodiments, needle protector 108 that can be removably attached to the base of a needle guard, with the lidded opening pointing away from the syringe barrel 102. In another embodiment, needle 126 may be placed in packaging separate from the other assembled components.

Needle protector(s) 108 and cap(s) 128 can be removably attached to the mixing/administration system 100 as packaged, and, in embodiments, needle 126 attached in their place.

FIG. 1B is a side view of an example of a needle end of a mixing/administration system that includes a cap, in accordance with one aspect of the disclosure. In embodiments, cap 128a is removably attached to needle protector 108 at end 130a of needle protector 108. Needle protector 108 covers needle 126a. Contents (not shown) of cap 128a are maintained in a sterile state by a seal formed between an interior circumference of cap 128a and an exterior circumference of needle protector 108. In embodiments, the connection of cap 128a to needle protector 108 forms a seal to enclose the contents of cap 128a (e.g., applicator material, and/or one or more cleansing, antimicrobial, antiseptic, disinfectant, or hemostatic agents), thus preventing leakage or evaporation.

FIG. 1C is a side view of an example of a needle end of a mixing/administration system includes a first cap removably attached to a second cap, in accordance with an aspect of the disclosure. In embodiments, first cap 132 is removably attached to needle protector 108 at end 130b of needle protector 108. Needle protector 108 covers needle 126b. In embodiments, first cap 132 and second cap 134 can be detachably coupled together at the narrower end of each cap 132, 134. In embodiments, first cap 132 and second cap 134 are attached or coupled via a seal or adhesive 144 to which each cap is attached. In embodiments, caps 132, 134 may be attached by heat seal that can be broken by hand or other seal that can be broken by hand. Cap 132 and cap 134 may be removed or detached from each other by, for example, twisting, pulling, snapping, or bending the one cap away from the other cap.

Figure 3A:
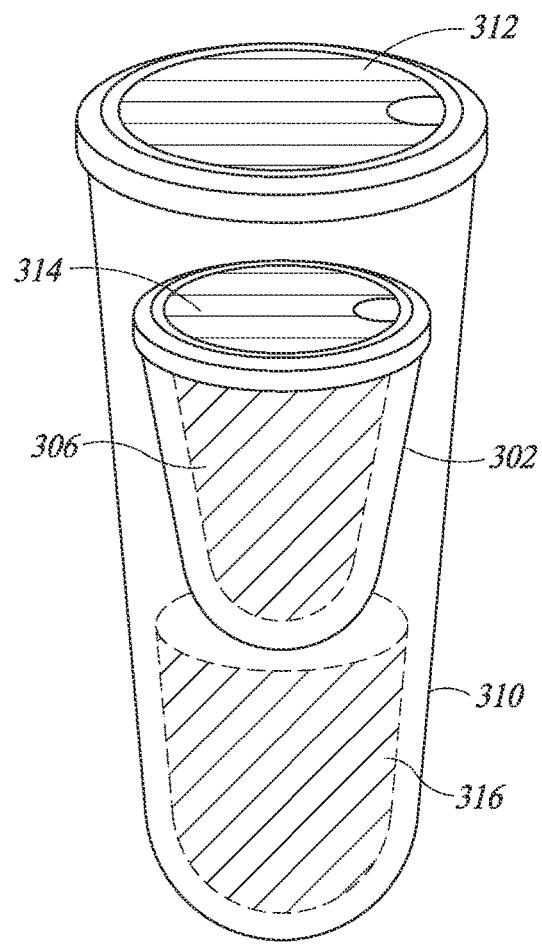
FIG. 3A is a perspective view of a sealed second cap that contains a sealed first cap, in accordance with an aspect of the disclosure.

In the configuration illustrated in FIG. 1C, contents (not shown) of cap 132 are maintained in a sterile state by a seal formed between interior circumference of cap 132 and exterior circumference of needle protector 108 and contents (not shown) of second cap 134 are maintained in a sterile state by removable protective lid 136. A receptacle within each cap may contain a permeable foam applicator material (e.g., as shown in FIG. 3A as 306, 316, etc.) that may be coated or filled with, for example, the same composition or different compositions comprising one or more cleansing, antiseptic antimicrobial, disinfectant, or hemostatic agents and/or different concentrations of such composition. In embodiments, at least one of caps 132, 134 may contain a bare applicator material. In embodiments, the connection of cap 132 to needle protector 108 forms a seal to enclose the contents of cap 132 (e.g., applicator material, and/or one or more cleansing, antimicrobial, antiseptic, disinfectant, or hemostatic agents), thus preventing leakage or evaporation.

FIG. 1D is a side view of an example of a needle end of a mixing/administration system that includes a second cap contained inside of a first cap, in accordance with an aspect of the disclosure.

In embodiments, second cap 140 is enclosed within first cap 138 by a seal formed between an interior circumference of cap 138 and an exterior circumference of needle protector 108 at end 130c of needle protector 108. Needle protector 108 covers needle 126c. In embodiments, contents of first cap 138 are maintained in a sterile state by a seal formed between an interior circumference of cap 138 and an exterior circumference of needle protector 108, thus preventing leakage or evaporation. In embodiments, contents of second cap 140 are maintained in a sterile state by removable protective lid 142, which can be removed after second cap 140 is removed from first cap 138.

Figure 2A:
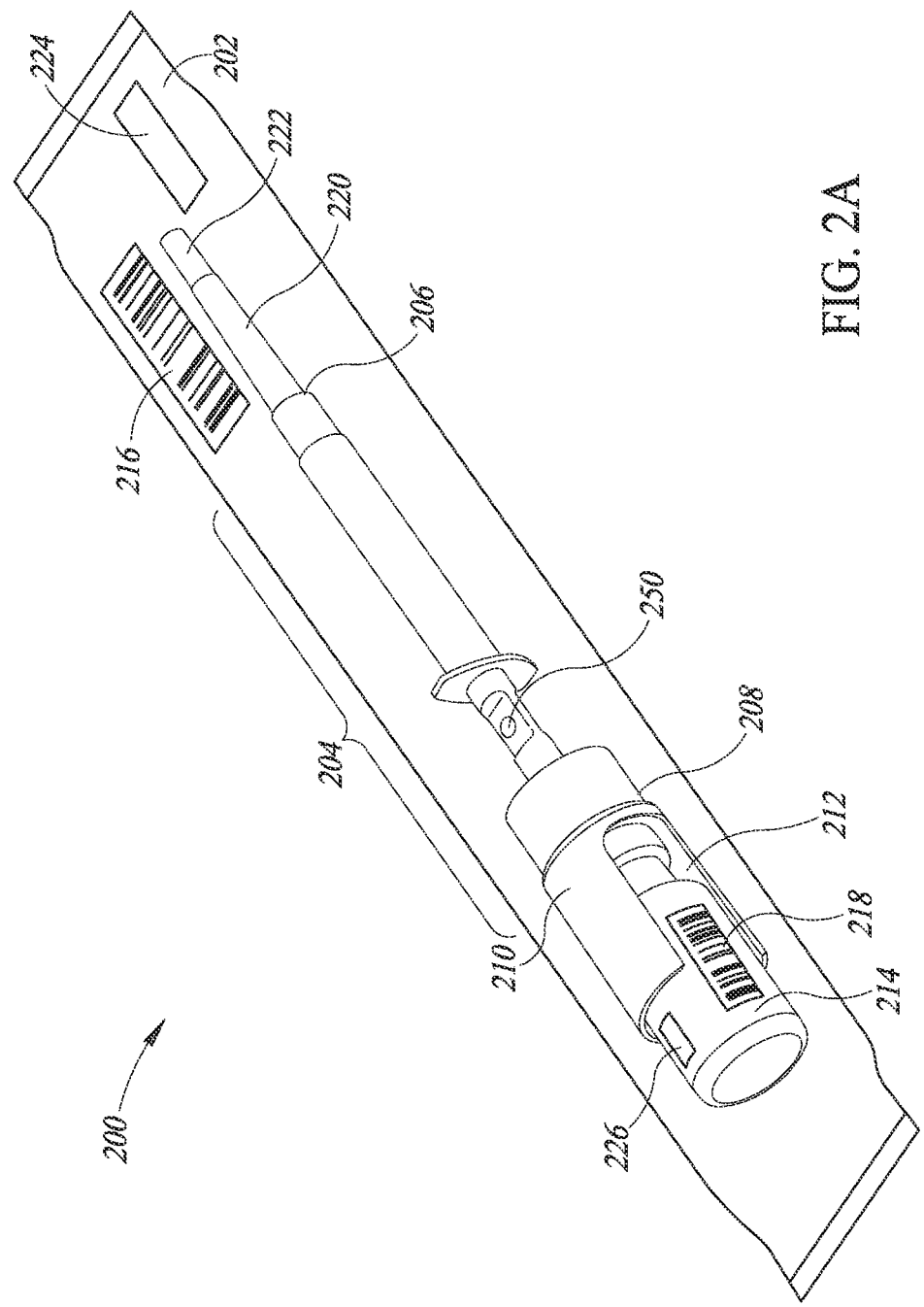
FIG. 2A is a perspective view of an example of a mixing/administration system that includes a tracking mechanism, packaging, and a dual-chamber syringe, in accordance with an aspect of the disclosure.
Figure 2B:
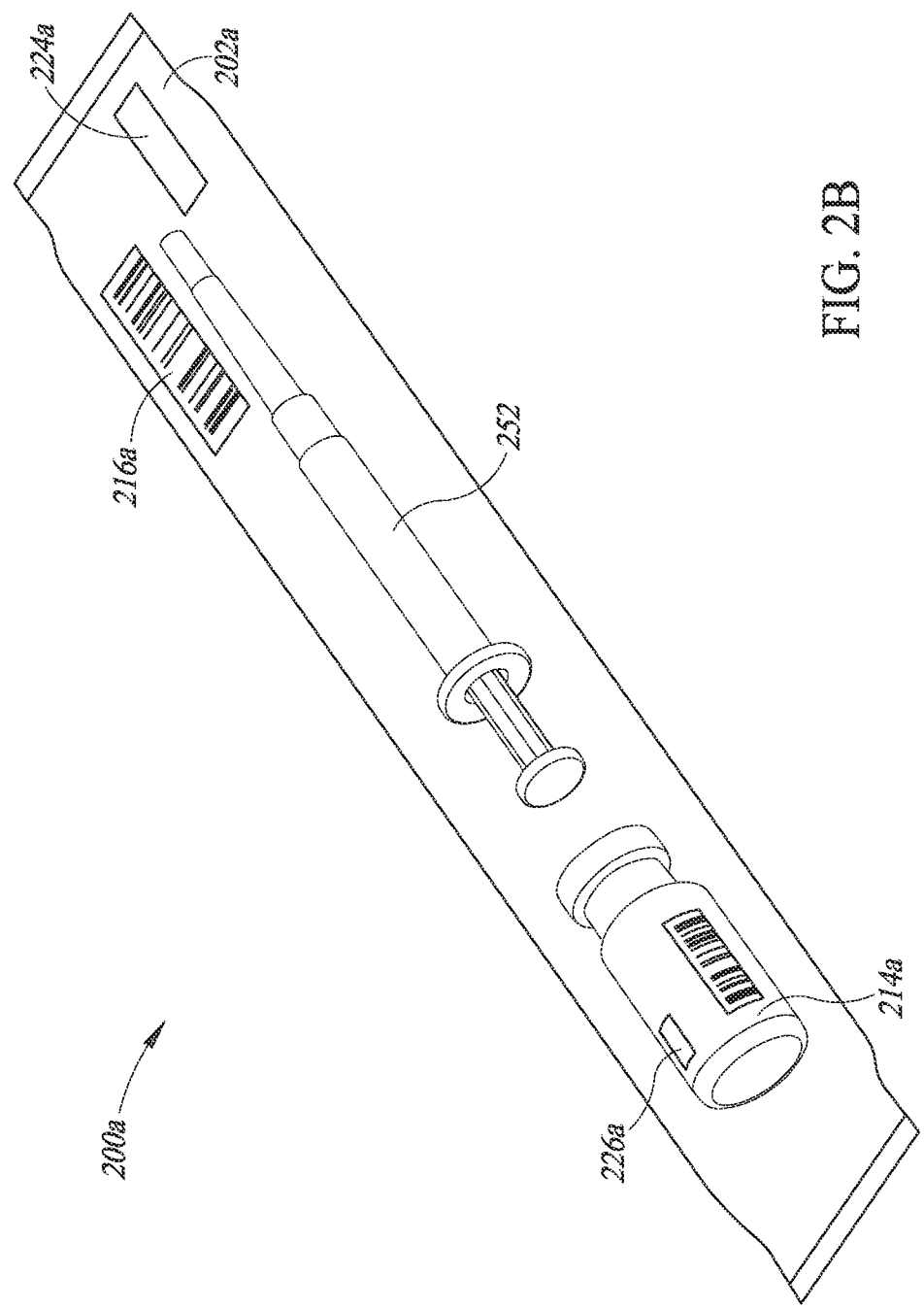
FIG. 2B is a perspective view of an example of a mixing/administration system that includes a tracking mechanism, packaging, and a generic syringe, in accordance with an aspect of the disclosure.

FIG. 2A illustrates the mixing-administration system 100 of FIG. 1 within packaging 202 (collectively, 200). FIG. 2B illustrates a generic syringe within packaging 202 (collectively, 200a).

In embodiments, the mixing-administration system can include packaging, a tracking mechanism, and any syringe. As discussed below, in the example illustrated in FIG. 2A, packaging, a tracking mechanism, and a particular syringe similar to the syringe in mixing-administration 100 are described, but in the embodiment illustrated in FIG. 2B, any syringe may be included.

FIG. 2A illustrates a piston 204 with first end 206 and opposing second end 208. Piston 204 has an internal fluid passage (not shown) which extends longitudinally from first end 206 to vial housing 210. Fluid passage through piston 204 and the vial penetrator (not shown in FIG. 2A) is controlled by way of valve 250, which is insertable into an opening in stem portion across fluid passageway (not shown). Vial housing 210 has internal sidewalls 212 which may be textured by, for example, providing raised features such as raised bumps along at least a portion of such internal sidewalls 212. Alternative raised features may be utilized such as ridges, ribs, etc. Texturing in internal sidewalls 212 may assist in providing a tight fit between the internal sidewalls 212 and a container or vial 214 provided within vial housing 210 and help retain the positioning of such container within vial housing 210. Further, the thickness of internal sidewalls 212 may be such to provide a tight fit with vial 214 (i.e. have an inner diameter only slightly larger than the largest outer diameter of the enclosed container) and be thin enough to allow the housing to fit within the syringe chamber.

After administration of a vaccine, at least some of the components of system 100 may be disposed of in packaging 202. In embodiments, packaging 202 may include only the compartments used to house the pre-injection components of the mixing/administration system. In another embodiment, packaging 202 may include additional compartment(s) for disposing of all or some of the system. In an example, the additional compartment is able to re-sheath used needle 126.

In embodiments, any of the caps described above and below may be placed in packaging 202 to receive needle 126, thus preventing accidental puncture or sticking of packaging 202, other objects, or individuals. Cap(s) 222 may be stored within the packaging 202, attached to the syringe components. In examples, cap(s) 222 may be sealed directly to the syringe body (e.g., on, or to the plunger, wings, or other portion of the syringe device). FIG. 2A illustrates cap(s) 222 attached to needle protector 220. In embodiments, cap(s) 222 may be packaged in a packaging 202 in a separate compartment (not shown) of the packaging. In other examples, cap(s) 222 may be sealed in a separate compartment by a separate removable film or cover.

In embodiments, packaging 202 can be waterproof. In an embodiment, packaging 202 can be opaque. In another embodiment, packaging 202 can be transparent.

Location 216 and/or location 218 represent locations for a label and/or locations at which information is printed.

Although shown on the vial 214 and on packaging 202, location(s) 216, 218 may be anywhere on the mixing-administration system 100. A single label at location 216, 218 (or printed information at a location 216, 218) may have different purposes. A plurality of labels at locations 216, 218 may each have the same purpose, or each have a different purpose. In embodiments, a single label is included, on the outside of packaging 202, at location 216

As illustrated in FIG. 2A, in embodiments, location 216 or location 218 can include a tracking mechanism (e.g., a barcode) that can be scanned and associated with a specific patient (alternatively referred to herein as "recipient") at the time of injection. In an example, a barcode may be placed on a label affixed at location 216 or location 218. In embodiments, data about the manufacture of the medicament is stored in association with the barcode. In an example, the barcode and the data about the manufacture are received by an application executing on a first user device. In an example, a scanner can be coupled to the first user device via a network. When the scanner scans the barcode, the barcode identifier is transmitted to the application on the first user device. The application can associate the barcode identifier with some or all of the manufacturing data. One or more servers connected to the first user device via the network can receive and store the data and the barcode identifier and can store the association between the data and the barcode identifier.

In embodiments, additional data can be associated with the barcode around the time of administration of the vaccine. A second user device can be used to collect the administration data, via another instance of the same application as is executing on the first user device, or via an instance of another application. Whichever application is used is able to communicate with the server(s). In an example, a second scanner can scan the barcode on the packaging 202 and transmit the barcode to an application executing on the second user device. In examples, the scanner can comprise one or more of a smartphone, handheld scanner, or other scanning device. Data associated with administration of the data can be input (manually or electronically) to the application in the same record as the barcode. Alternatively, the administration data can be received by another application executing on the second user device and the other application (or the server(s)) can later associate the barcode with the administration data.

The administration data can include, but is not limited to, at least one of an identity/name/identifier of a patient, date of birth of a patient, address of a patient, time and/or date of the injection given to a patient, geolocation of the injection, HIV status of the patient and whether HIV is being treated, a picture of a patient, demographic information of a patient, identity and/or location of an individual and/or entity administering the injection, adverse reactions of the patient, allergies of the patient to the medicament or other components of the vaccine, dosage number, vital signs of a patient, diagnoses or other health history of a patient, etc. Additional examples of administration data are discussed above and below.

The server(s) receive, via the application collecting the information on the second user device, the administration data in association with the barcode identifier and, via the barcode identifier, store the administration data. The administration data can be sent to the server(s) via a third-party device. The third-party device can process the administration data (e.g., pseudonymizes, anonymizes, encrypts, filters, formats, etc.) In embodiments, the user device and/or the servers can perform these processing functions. The server(s) can receive and store manufacturing data and administration data associated with other barcodes attached to other packaging encasing other medicaments. Additional discussion of this process is discussed below with respect to FIG. 5.

In embodiments, packaging 202 or vial 214 can include a viability indicator 224. Additionally or alternatively, vial 214 can include a viability indicator 226. In embodiments, viability indicator 224, 226 is incorporated into the tracking mechanism at location 216, 218. A viability indicator can indicate exposure of the packaging 202 or mixing/administration system 100 to certain temperatures or light. In an example, the viability indicator 224, 226 can comprise a heat exposure indicator and the heat exposure indicator can be included as part of the label). In embodiments, the viability indicator 224, 226 and/or label including the heat exposure indicator can change color to indicate high ambient temperatures. In an example, a heat exposure indicator may change color if the package deviates in temperature from approximately 5-8 degrees Celsius. In embodiments, Vaccine Vial Monitor ("VVM") may be used. VVM may comprise a label that is placed on the packaging of the mixing/administration system that includes a heat exposure indicator that changes color upon exposure to a certain temperature and/or light. In an example, the color blue indicates excessive temperature or light that could inactivate the vaccine, and light-blue indicates that the package was exposed to high temperature or light, though not potentially inactivating levels. In embodiments, a VVM label is placed on opaque packaging that maintains the vaccine and prevents exposure to ultraviolet light.

In embodiments, temperature may be monitored to check if the temperature of the mixing/administration system is—or has been—too cold. That is, when the temperature is below about 4 degrees Celsius, the vaccine may be inactivated. Low temperatures around this temperature may result in freezing and inactivation of live, attenuated, viruses in vaccines and degradation of biologicals, and other medicaments. Various methods could keep track of inactivating low temperatures, including via a monitor on the packaging. In embodiments, a printout of temperatures over time may, or a graph showing the same, may be collected by a monitor at the site of the container, or a digital readout associated with a monitor may be generated, or data may be transmitted via a network from the container to one or more servers.

FIG. 2B illustrates an embodiment of a mixing/administration system similar to the system of FIG. 2A, including packaging 202a, vial 214a, location 216a, viability indicator 224a and viability indicator 226a, but including a generic syringe 252.

Figure 3B:
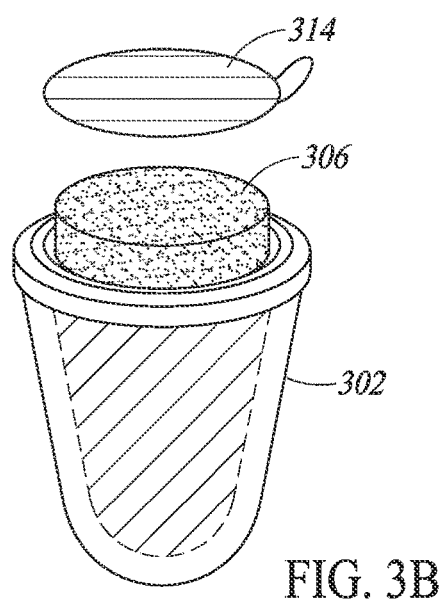
FIG. 3B is a perspective view of the first cap illustrated in FIG. 3A in an unsealed state, in accordance with an aspect of the disclosure.
Figure 3C:
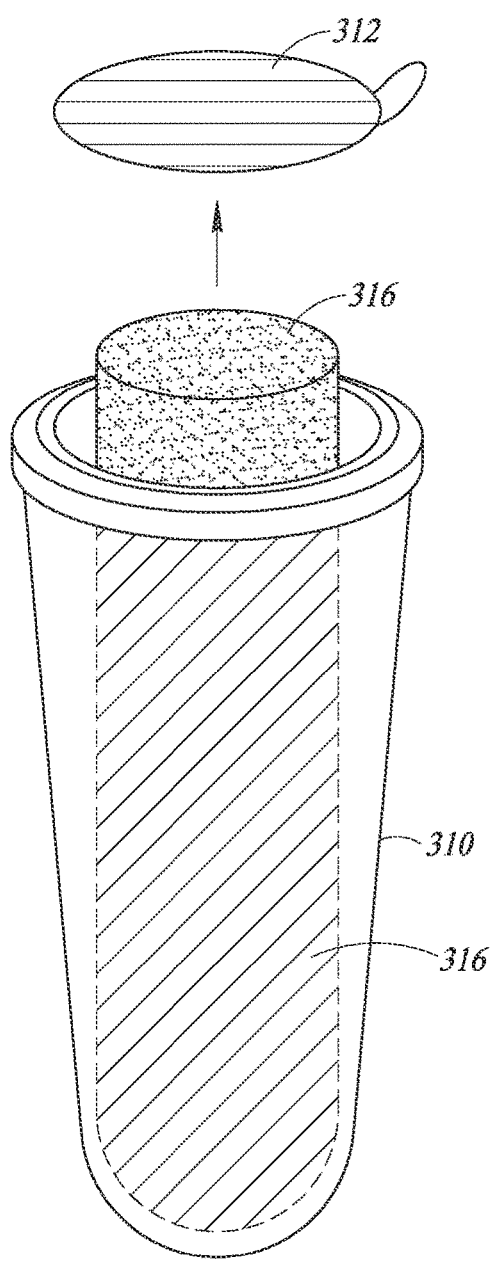
FIG. 3C is a perspective view of the second cap illustrated in FIG. 3A in an unsealed state, in accordance with an aspect of the disclosure.

FIGS. 3A, 3B, and 3C illustrate several aspects of caps that may be used with the mixing/administration system.

FIG. 3A is a perspective view of a sealed second cap that contains a sealed first cap, in accordance with an aspect of the disclosure. FIG. 3A illustrates two caps 302, 310, as a first cap 302 within a second cap 310. In embodiments, first cap 302 and/or second cap 310 are functional to be used for sterile compression to stop bleeding at the injection site and/or for application of one or more cleansing, antiseptic, antimicrobial, disinfectant, or hemostatic agents. As described above, in embodiments, first cap 302 and second cap 310 include an applicator material (306 and 316, respectively) disposed within a receptacle or interior cavity of each cap prior to use.

In embodiments, each cap 302, 310 may be sealed by a removable protective lid (314, 312 respectively) over an interior cavity that contains an applicator material (316, 306 respectively). In embodiments, applicator material 306, 316 can be dry or can include a liquid composition comprising one or more cleansing, antimicrobial, antiseptic, disinfectant, or hemostatic agents. In embodiments, applicator material 306 of first cap 302 may include a composition comprising one or more cleansing, antimicrobial, antiseptic, disinfectant, or hemostatic agents and/or a concentration of the composition that is different from composition of applicator material 316 of second cap 310.

In embodiments, removable protective lid 312, 314 includes a tab that can be pulled to remove the removable protective lid 312, 314 from the rim of the cap. In embodiments, when cap 302, 310 is sealed, the applicator material 306, 316 inside the cap may be in a state of compression. In embodiments, when removable protective lid 314 is removed from first cap 302, applicator material 306 may expand and/or protrude from the interior cavity of first cap 302 for applying a composition comprising one or more cleansing, antiseptic, antimicrobial, disinfectant, or hemostatic agents for cleansing and/or stopping bleeding at an injection site. In embodiments, when removable protective lid 312 is removed from second cap 310, the applicator material 316 may expand and/or protrude from the interior cavity of second cap 310 for applying a composition comprising one or more cleansing, antiseptic, antimicrobial, disinfectant, or hemostatic agents for cleansing and/or stopping bleeding at an injection site.

FIG. 3B is a perspective view of the first cap illustrated in FIG. 3A in an unsealed state, in accordance with an aspect of the disclosure. FIG. 3B illustrates first cap 302 that includes applicator material 306 expanding outside of first cap 302 after removable protective lid 314 is removed. In embodiments, applicator material 306 can extend beyond the plane of the opening of cap 302 after removable protective lid 314 affixed to the rim of first cap 302 is removed. In embodiments, first cap 302 is tapered, and removable protective lid 314 attaches at the widest point of first cap 302.

FIG. 3C is a perspective view of the second cap illustrated in FIG. 3A in an unsealed state, in accordance with an aspect of the disclosure. FIG. 3C illustrates second cap 310 that includes applicator material 316 expanding outside of second cap 310 after removable protective lid 312 is removed. In embodiments, applicator material 316 can extend beyond the plane of the opening of second cap 310 after removable protective lid 312 affixed to the rim of second cap 310 is removed. In embodiments, second cap 310 is tapered, and removable protective lid 312 attaches at the widest point of second cap 310.

In embodiments, applicator material 306, 316 is a permeable foam or sponge material that may be coated or impregnated with a composition comprising one or more cleansing, antimicrobial, antiseptic, disinfectant, or hemostatic agents such as compositions described in the preceding section. In other embodiments, applicator material 306, 316 may be dry or bare and not be coated or impregnated. Example materials for the composition of the applicator material may include, but are not limited to starch polymer, cellulosic gel, polyurethane, silicon, silicon rubber, polyethylene, polypropylene, thermoplastic elastomer, or mixtures thereof.

In embodiments, applicator material 306, 316 may include, but is not limited to, different surface treatments (e.g., siping, slitting, etc.), surface finishes (e.g., macro-, micro-, or nano-structures, etc.), and/or contours (e.g., rounded, ribbed, protrusions, fingers, etc.) to provide cleaning and/or scrubbing and/or hemostatic effectiveness. In embodiments, applicator material 306 in first cap 302 may be configured similar to applicator material 316 in second cap 310 (e.g., with the same surface treatments, finishes and/or contours). However, in other embodiments, applicator material 306 in first cap 302 may be configured with different surface treatments, finishes and/or contours than applicator material 316 in second cap 310.

In embodiments, applicator material 306, 316 may take on a variety of shapes and/or sizes. The shape and/or size of applicator material 306 may be the same or different from the shape and/or size of applicator material 316. In embodiments, applicator material 306 and/or applicator material 316 may have a shape that is substantially similar to the shape of the receptacle of the corresponding cap.

Applicator material 306, 316 may be applied to a surface. Applicator material 306, 316 may be soaked with a composition comprising one or more cleansing, antiseptic, antimicrobial, disinfectant, or hemostatic agents (not shown) which may be used to cleanse or sanitize surfaces before or after the injection, or stop bleeding at the injection site after injection. In embodiments, applicator material 306 and/or applicator material 316 may be used for sterile compression to stop bleeding at the injection site.

The one or more cleansing, antiseptic, antimicrobial, disinfectant, or hemostatic agents comprising a composition may be in a liquid form or a gel form, and may be combined with one or more carriers or diluents, depending on the needs of a specific application. For example, if the composition is used as a cleansing agent, the composition may be in a liquid form. In that case, the concentration of the various agents may depend on, for example, a desired level of sanitation and/or disinfection, whether the composition is being applied directly to living tissue or to a medical device, and/or to avoid irritation of tissue to which the composition will be applied directly or indirectly (e.g., via a medical device to which the composition is or was applied).

In embodiments, a composition described herein that includes an antimicrobial agent can be referred to as an antimicrobial composition. In embodiments, an antimicrobial composition may include water ($H_2O$), a strong and non-toxic chelating agent such as ethylenediaminetetraacetic acid (EDTA) (e.g., disodium EDTA, calcium disodium EDTA, magnesium EDTA, potassium EDTA, gallium EDTA, etc.) or sodium citrate (or acids, salts, derivatives, or other forms of EDTA or sodium citrate); a short-chain monohydric alcohol (e.g., ethanol with a molecular formula of $C_2H_5OH$ and an empirical formula of $C_2H_6O$); and a strong, small molecule oxidizing agent such as hydrogen peroxide ($H_2O_2$). In an example, an antimicrobial composition may include water, EDTA, ethanol, and hydrogen peroxide. Additional ingredients may include thickeners, gellants, surfactants, foamers and/or foam stabilizers. However, in other examples, other antimicrobial compositions may be used in combination with the applicator materials and devices described in this disclosure.

In embodiments, an antimicrobial composition of the present application may be applied to hands to reduce or prevent the transmission of bacterial, fungal, viral, and parasitic diseases, such as in a clinical environment. The antimicrobial composition may provide a means by which biofilms as formed by bacterial and fungal organisms are disrupted and the embedded organisms in the biofilm, whether they are biofilm formers or present by accidental inclusion, entrapment or otherwise, are killed or rendered non-viable and/or otherwise non-threatening. The antimicrobial composition may provide a means by which bacterial and yeast spores are either killed outright in the spore stage, or are rendered ineffective by being unable to germinate, or by germination followed by rapid killing before their pathogenic potential is expressed. The antimicrobial composition may provide a means by which quorum sensing (QS) mechanisms used by biofilm forming microorganisms is interrupted. While these mechanisms vary from organism to organism, and gram-positive organisms use a somewhat different QS system from gram-negative, in all cases there is a molecule or series of molecules which provide the QS function. In many cases, these are protein molecules that are potentially susceptible to structural changes by reaction with the antimicrobial composition of the present application. Reactions such as hydrolysis, alcoholysis, esterification, transesterification, oxidation, protein denaturation, or chelation of both free ions and partially bound cations are likely possibilities. Substances which are targets for hydrolytic or alcoholytic destruction or disruption are, for example, acyl-homoserine lactones (AHL's, the QS molecules of gram-positive biofilm formers), and other lactone or ester components of gram-positive bacteria. Bio films area are also known to be disrupted by chelators, which it is believed, results from the binding effect of the chelator on divalent, trivalent, or other cations necessary for the formation of the biofilm. Inclusion of one or more chelators (e.g., EDTA, etc.), provides this function to an antimicrobial composition of the present application.

In addition to providing disinfection at the time of the application, an antimicrobial composition described herein may also provide a lasting barrier against contamination. For example, even after volatile constituents of the composition (e.g., water, alcohol, hydrogen peroxide, etc.) have evaporated, the chelating agent may remain on the treated surfaces (e.g., multiple use vial or port cleaning/protecting device, stethoscope, fingers, other tissue, etc.) as a barrier that will provide antibacterial, antifungal or sporicidal (e.g., preventing germination of the spores), anti-parasitic, spermicidal or spermiostatic (e.g., decrease the motility of spermatozoon) and antiviral qualities. By robbing the environment of components (e.g., iron, magnesium, and manganese) that are needed for the bacteria, spores, parasites, fungus, and viruses to reproduce, the chelating agent provides a lasting defense to contamination even after other constituents of the antimicrobial composition have evaporated. Furthermore, the hydrogen peroxide in the antimicrobial compositions may induce a charge on a surface of materials (e.g., silicone materials) to which the antimicrobial compositions are applied, which make the materials more resistant to bacteria or other microorganisms.

In embodiments, an antimicrobial composition described herein may also provide a visual indication of contamination when applied to a surface or material. Such indication may allow users to identify and clean surfaces to prevent infection.

In embodiments, an antimicrobial composition described herein may have less EDTA within cap 302, 310 and/or applicator material 306, 316. For example, in embodiments in which cap 302, 310 is used to apply pressure to stop bleeding after an injection, the EDTA level in the composition is reduced because the EDTA could prevent, not cause, coagulation at the injection site.

In embodiments, a cap may be used to clean, sanitize, and/or disinfect a surface (e.g., skin or tissue) prior to using the mixing/administrative system. For example, first cap 302 and/or second cap 310 may be used to clean an injection site prior to using the mixing/administrative system at the injection site. In embodiments, first cap 302 and/or second cap 310 may be applied to the mixing/administrative system to disinfect the syringe prior to use. Additionally or alternatively, first cap 302 and/or second cap 310 may be applied to a vial of medicament or diluents to disinfect the vial prior to use, between uses, and/or during storage.

In embodiments, one of the caps may include applicator material that protrudes from the receptacle of the cap in use, while a second cap may comprise a cap having applicator material that fits completely within and/or is recessed in a receptacle in the cap when in use. In that case, the cap with the protruding applicator material may be used to clean a surface (e.g., an injection site) and the second cap with the recessed applicator material may be used to cover and protect a port, vial, needle, or other component.

Figure 4:
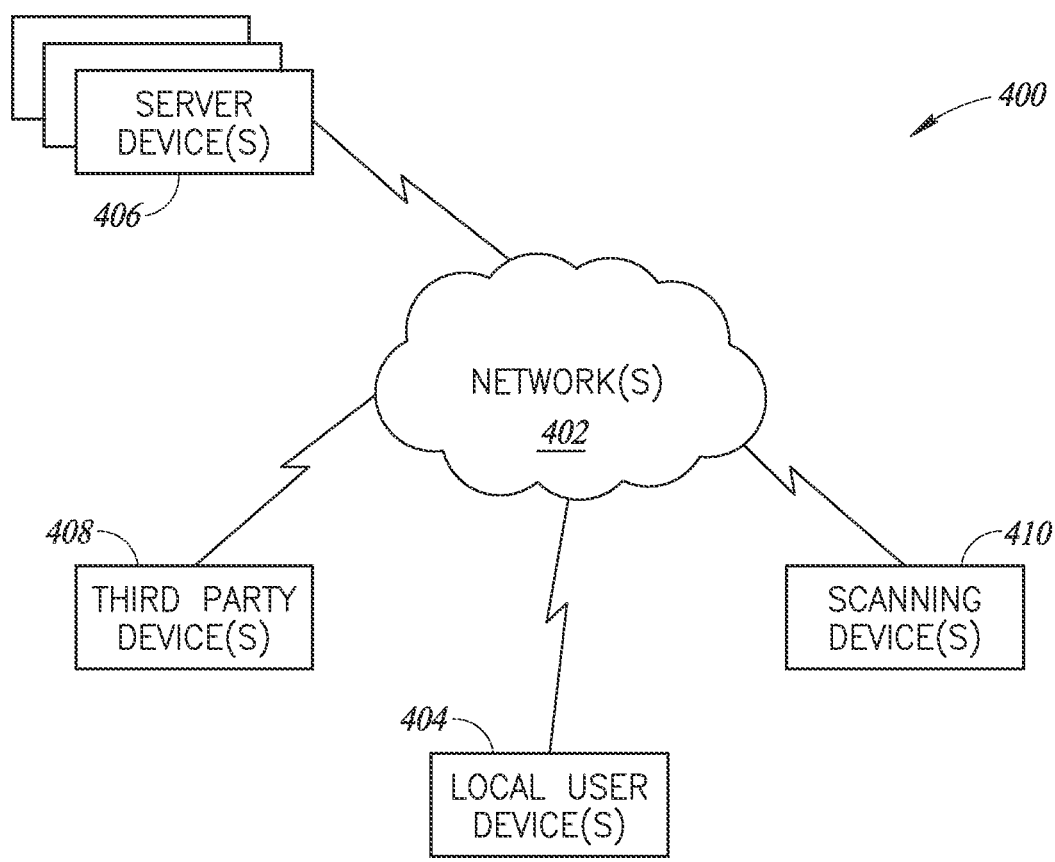
FIG. 4 illustrates an example operating environment in which techniques described herein may be implemented.

FIG. 4 illustrates an example operating environment 400 in which techniques described herein may be implemented. The example operating environment 400 may include one or more local user device(s) 404 (also referred to herein a "user device(s)" or "local device(s)"). The one or more user device(s) 404 may be coupled to one or more server device(s) 406 (also referred to herein a "server(s)" or "one or more servers" or, collectively, a "server system"), across one or more network(s) 402. In examples, the operating environment 400 may include one or more third-party device(s) 408 (also referred to herein as "third-party device(s)") and/or one or more scanning devices 410. In embodiments, a scanning device 410 can be associated with or incorporated in the user device(s) 404).

For simplicity of reference, components throughout this disclosure may be referred to in the singular form and in connection with a single generalized reference numeral. For example, the one or more user device(s)) (i.e., the plural form) may be referred to as a user device (i.e., the singular form). Nonetheless, it should be understood that use of the singular form may include the plural form in certain implementations.

One or more of the user device 404 or the server 406 can include any type of computing device that is generally configured to perform an operation. For example, one or more of the user device or the server can be implemented as a laptop computer, a desktop computer, a server, a smart phone, an electronic reader device, a mobile handset, a personal digital assistant (PDA), a portable navigation device, a portable gaming device, a tablet computer, a watch, a portable media player, a television, a set-top box, a computer system in a car, an appliance, a camera, a robot, a hologram system, a home-based computer system (e.g., intercom system, home media system, etc.), a projector, an automated teller machine (ATM), a pair of glasses with computing capabilities, and so on.

Figure 5:
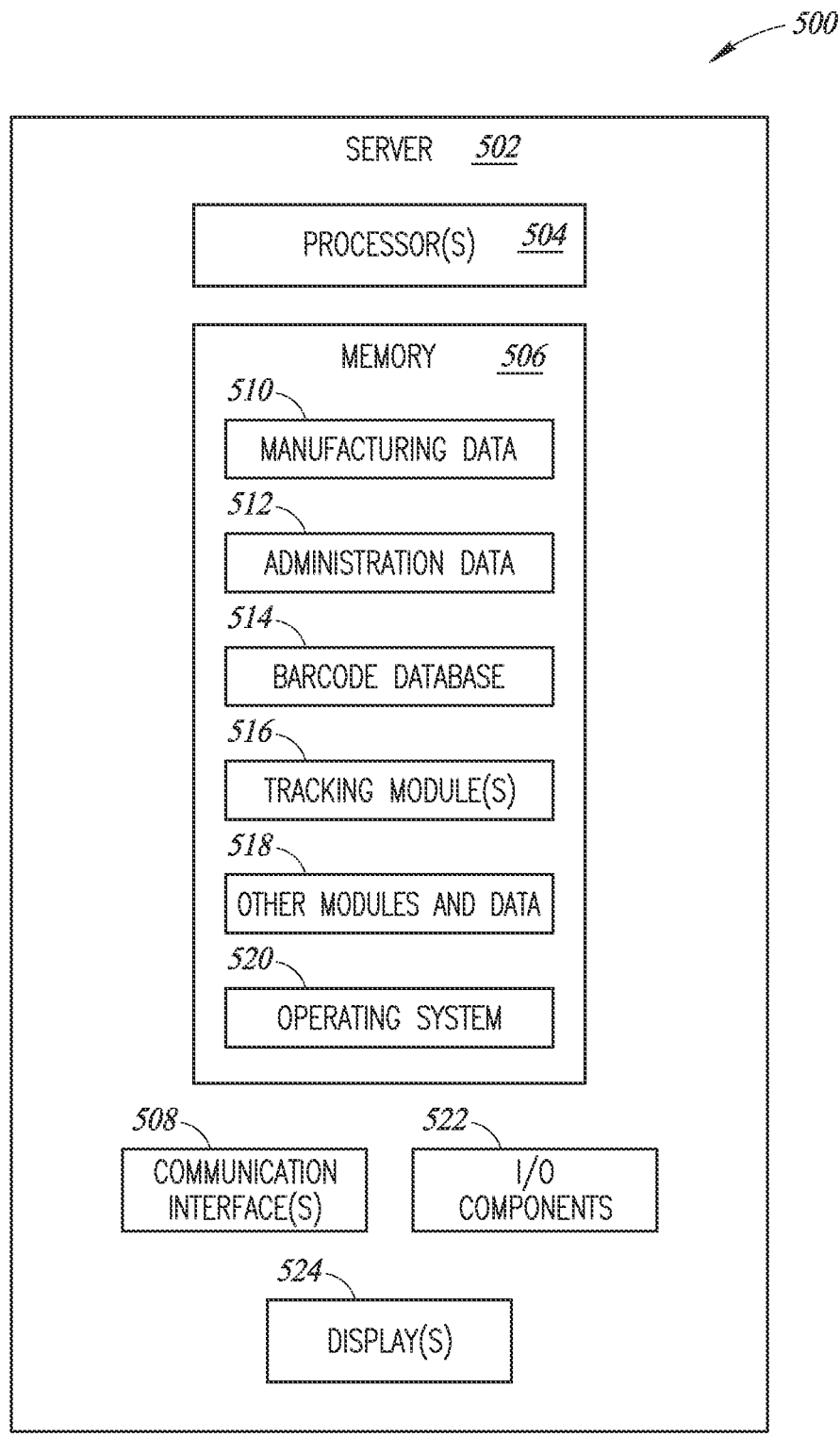
FIG. 5 illustrates select components of an example server system.

FIG. 5 illustrates select components of an example server system 500 including server 502.

In an example, operating environment 400 of FIG. 4 can include a server system 500. The server system 500 can be used in association with the tracking mechanism included in embodiments of this disclosure. The server system 500 is implemented as cloud-based computing services hosted, for example, on one or more servers 502. The server(s) 502 may be arranged in any number of ways, such as server farms, stacks, and the like that are commonly can be used in data centers. The cloud services generally refer to a network accessible platform implemented as a computing infrastructure of processors, storage, software, data access, and so forth that is maintained and accessible via a network such as the Internet. Cloud services do not require end-user knowledge of the physical location and configuration of the system that delivers the services. Expressions associated with cloud services include "on-demand computing", "software as a service (SaaS)", "platform computing", "network accessible platform", and so forth.

Server 502 can store, analyze, and report data, including but not limited to vaccine manufacturing data 510 and administration data 512. Server 502 may include one or more processors 504, memory 506, one or more communication interfaces 508, one or more displays 524, one or more input/output (I/O) components 522, or any combination thereof.

The processor(s) 504 may be a single processing unit or a number of processing units, and may include single or multiple computing units or multiple processing cores. The processor(s) 504 can be configured to fetch and execute computer-readable instructions stored in the memory 506 or other computer-readable media. A processor 504 of server 502 can itself include one or more processors or processing cores. For example, the one or more processors can be implemented as one or more microprocessors, microcomputers, microcontrollers, digital signal processors, central processing units, state machines, logic circuitries, and/or any devices that manipulate signals based on operational instructions. In examples, the one or more processors can be one or more hardware processors and/or logic circuits of any suitable type specifically programmed or configured to execute the algorithms and processes described herein.

Depending on the configuration of server 502, memory 506 can be an example of computer storage media and can include volatile and nonvolatile memory and/or removable and non-removable media implemented in any type of technology for storage of information such as computer-readable processor-executable instructions, data structures, program modules or other data as discussed above. For example, memory can include, but is not limited to, RAM, ROM, EEPROM, flash memory, solid-state storage, magnetic disk storage, optical storage, and/or other computer-readable media technology. Further, in an example, server 502 can access external storage, such as RAID storage systems, storage arrays, network attached storage, storage area networks, cloud storage, or any other medium that can be used to store information and that can be accessed by the one or more processors directly or through another computing device or network. Accordingly, server 502 can include computer storage media able to store instructions, modules, or components that can be executed by the one or more processors. Further, when mentioned, non-transitory computer-readable media and computer storage media exclude media such as energy, carrier signals, electromagnetic waves, and signals per se.

Memory 506 may be a type of computer-readable storage media and may include tangible non-transitory storage media. In addition, in an example, the computer readable media can be associated with transitory computer-readable signals (in compressed or uncompressed form). Examples of computer-readable signals, whether modulated using a carrier or not, include, but are not limited to, signals that a computer system hosting or running a computer program can be configured to access, including signals downloaded through the internet or other networks.

Memory 506 can be used to store and maintain any number of functional components that are executable by the processor(s) 504. In some implementations, these functional components include instructions or programs that are executable by the one or more processors and that, when executed, implement operational logic for performing the actions and services attributed above to server 502.

Furthermore, memory can include one or more additional functional components, such as operating system (not shown) for controlling and managing various functions of server 502 and for enabling basic user interactions. In addition, memory can store data, data structures and the like, that are used by the functional components.

Depending on the type of server, memory can also optionally include other functional components and data, such as other modules and data 518, which can include one or more of programs, drivers, etc., and the data used or generated by the functional components. Further, server 502 can include many other logical, programmatic, and physical components, of which those described are merely examples that are related to the discussion herein.

The term "module" is intended to represent example divisions of the software for purposes of discussion and is not intended to represent any type of requirement or required method, manner, or necessary organization. Accordingly, while various "modules" are discussed, their functionality, similar functionality, or both, could be arranged differently (e.g., combined into a fewer number of modules, broken into a larger number of modules, etc.). The modules can include computer instructions/code that can be stored in the memory and can be executable by the one or more processors.

The server 502 can be configured with, or otherwise include, one or more tracking module(s) 516. In examples, the tracking module(s) 516 provide functionality for carrying out the techniques described in this disclosure.

Tracking module(s) 516 can be maintained in memory 506 and executed on the processor(s) 504 to perform acts. The acts can include one or more of receiving a user's request related data in memory 506 and, in response to receiving the request, causing to be presented an aggregation of information. Additionally or alternatively, the acts can include receiving, from one or more user devices, and storing, administration data 512 and manufacturing data 510 in association with a barcode identifier. Additionally or alternatively, the acts can include sharing and/or publishing analysis and/or reports based at least in part on the manufacturing data 510 and/or administration data 512. Sharing and publishing can be to user devices or to other devices.

In an example, the server 502 can include one or more display 524. Depending on the type of computing device(s) used as the server, a display 524 can employ any suitable display technology. For example, a display 524 can be a liquid crystal display, a plasma display, a cathode ray tube (CRT) monitor, a light emitting diode display, an OLED (organic light-emitting diode) display, an electronic paper display, or any other suitable type of display able to present digital content thereon. In an example, a display 524 can have a touch sensor associated with the display 524 to provide a touchscreen display configured to receive touch inputs for enabling interaction with a graphic interface presented on the display 524. Accordingly, implementations herein are not limited to any particular display technology. Alternatively, in an example, server 502 may not include display, and information can be presented by other means, such as aurally.

In an example, the server 502 can include one or more I/O component(s) 522 that can be configured to allow interfacing with the server 502 via one or more I/O devices. The I/O component(s) 522 can provide an interface for devices including one or more of display(s), speakers (not shown), a microphone (not shown), a keyboard (not shown), a mouse (not shown), a camera (not shown), a scanner or optical reader (not shown), a touchpad (not shown), a haptic output device (not shown), or any combination thereof.

In an example, the server 502 can include one or more communication interface(s) 508 that can include one or more interfaces and hardware components for enabling communication with various other devices, such as over network(s) or directly. For example, communication interface(s) 508 can enable communication through one or more networks, which can include, but are not limited to any type of network known in the art such as a local area network or a wide area network, such as the Internet, and can include a wireless network, such as a cellular network, a local wireless network, such as Wi-Fi and/or close-range wireless communications, such as Bluetooth®, BLE, NFC, RFID, a wired network, or any other such network, or any combination thereof, etc. A network can include both wired and/or wireless communication technologies, including Bluetooth®, BLE, Wi-Fi and cellular communication technologies, as well as wired or fiber optic technologies, etc. Components used for such communications can depend at least in part upon the type of network, the environment selected, or both.

Server 502 can additionally include other devices including a GPS device (not shown) that is able to indicate location information. Further, server 502 can include one or more sensors (not shown), such as an accelerometer, gyroscope, compass, proximity sensor, camera, microphone, and/or a switch, as discussed above. Additionally, server 502 can include various other components that are not shown, examples of which include removable storage, a power source, such as a battery and power control unit, a printer, and so forth.

In embodiments, server 502 can receive, via a network, and stores, in memory 506, manufacturing data 510 from device(s) associated with manufacturing mixing/administration system(s), including but not limited to medicaments, packaging, vials, syringes, and/or any other components mixing/administration system(s). Manufacturing data 510 can include at least one of a lot number for at least one of the medicament, a vial containing the medicament, or a diluent included in the syringe; a date and/or time of manufacture of at least one of the medicament, the vial, or the diluent; a location of manufacture of at least one of the medicament, the vial, or the diluent; a manufacturer of at least one of the medicament, the vial, or the diluent; a chemical composition of at least one of the medicament or diluent and/or chemical composition and/or other information about individual components comprising the medicament or diluent; packaging information of at least one of the medicament or the vial; shipping information of at least one of the medicament or the vial; dosage information of the medicament; or an expiration date of the medicament or diluent. In embodiments, manufacturing data can additionally include a lot number for the syringe; a manufacturer of the syringe; a date of manufacture or packaging of the syringe; a time of manufacture or packaging of the syringe; a location of manufacture of the syringe; components of the syringe; and/or component manufacturing data;

In embodiments, server 502 can receive receives administration data 512, which can include at least one of an identity/name/identifier of a patient, date of birth of a patient, address of a patient, time and/or date of the injection given to a patient, geolocation of the injection, HIV status of the patient and whether HIV is being treated, a picture of a patient, demographic information of a patient, identity and/or location of an individual and/or entity administering the injection, adverse reactions of the patient, allergies of the patient to the medicament or other components of the vaccine, dosage number, vital signs of a patient, diagnoses or other health history of a patient, etc.

Each of administration data 512 and manufacturing data 510 is associated with a barcode identifier. In embodiments, a barcode affixed to packaging of a medicament can be scanned in conjunction with entry of data associated with that medicament. The barcode identifier is transmitted with an association to data 510, 512. In examples, the data 510, 512 and the barcode identifier can be transmitted to the server from a scanning device or a user device communicatively coupled to the scanning device. In other examples, the data 510, 512 the scanning device and user device are the same device (e.g., a smartphone).

In embodiments, server 502 can maintain one or more databases in memory 506 for storing the data 510, 512 in association with the barcode identifier and/or can maintain one or more databases in memory storing the data 510, 512 and a barcode database 514 that stores barcode identifiers and associations to data 510, 512. In embodiments, there is no separate barcode database. In an embodiment illustrated in FIG. 5, memory 506 includes at least manufacturing data 510, administration data 512, and barcode database 514. In embodiments, manufacturing data 510, administration data 512, and barcode database 514 can be stored as part of or in association with tracking module(s) 516.

Additional information may be input manually at server 502 or received from a user device or scanning device. The scanning device and/or user device (s) need not have a wireless connection at the time of the scan and can later upload the data collected as part of the scan. The scanning device may upload the data directly to server 502 or may transmit the data to a local user device that uploads the data to the server 502. The scanning device and local user device can be a same device. Administration data 512 can be sent to a third-party device, and the third-party device send the administration 512 (in embodiments, after processing) to server 502.

In embodiments, a photograph (for example, taken with a smartphone or other device) of hard copy information such as patient data, provider data, date, time, etc., may be received by a user device and associated with a barcode identifier. In an example, an application executing on the user device can receive the photograph and the barcode identifier in a same record. The server 502 may then receive and store the photograph in association with the barcode identifier (e.g., as administration data 512). The hard copy information from the photograph may be stored as-is and/or an optical character recognition process may be performed.

In embodiments, a viability indicator as described above may be scanned simultaneously or sequentially to scanning a barcode. In embodiments, indication(s) from the viability indicator may be separately entered at the user device. In embodiments, indication(s) from the viability indicator may be received electronically as part of the scan of the barcode.

Having received administration data 512 and manufacturing data 510, both associated with the barcode identifier, server 502 may respond to requests for information about the patient, medicament, geolocation, or any other of the data or information collected. In an example, the server 502 may analyze data and respond to a request for all injections of a certain lot number of a medicament. In another example, the server may respond to a request for all injections administered in a certain geographic region during a period of time. However, information requested and provided by the server 502 can include any information or analysis of information derived from administration data 512 and/or manufacturing data 510 and/or other information received by server 502 from any source.

In an example, operating environment 400 can include one or more user device(s) 404. A user device can include one or more processors, memory, one or more operating systems, one or more tracking module(s), other modules and data, one or more displays, one or more input/output (I/O) components, one or more communication interface(s), or any combination thereof.

The processor(s) of the user device may be a single processing unit or a number of processing units and may include single or multiple computing units or multiple processing cores. The processor(s) can be configured to fetch and execute computer-readable instructions stored in the memory or other computer-readable media. A processor of the user device can itself include one or more processors or processing cores. For example, the one or more processors can be implemented as one or more microprocessors, microcomputers, microcontrollers, digital signal processors, central processing units, state machines, logic circuitries, and/or any devices that manipulate signals based on operational instructions. In an example, the one or more processors can be one or more hardware processors and/or logic circuits of any suitable type specifically programmed or configured to execute the algorithms and processes described herein.

Depending on the configuration of the user device, the memory of the user device can be an example of computer storage media and can include volatile and nonvolatile memory and/or removable and non-removable media implemented in any type of technology for storage of information such as computer-readable processor-executable instructions, data structures, program modules or other data as discussed above. For example, memory can include, but is not limited to, RAM, ROM, EEPROM, flash memory, solid-state storage, magnetic disk storage, optical storage, and/or other computer-readable media technology. Further, in an example, the user device can access external storage, such as RAID storage systems, storage arrays, network attached storage, storage area networks, cloud storage, or any other medium that can be used to store information and that can be accessed by the one or more processors directly or through another computing device or network. Accordingly, the user device can include computer storage media able to store instructions, modules, or components that can be executed by the one or more processors. Further, when mentioned, non-transitory computer-readable media and computer storage media exclude media such as energy, carrier signals, electromagnetic waves, and signals per se.

Modules of the user device can include computer instructions/code that can be stored in the memory and can be executable by the one or more processors of the user device. Memory of the user device can be associated with transitory computer-readable signals (in compressed or uncompressed form). Examples of computer-readable signals, whether modulated using a carrier or not, include, but are not limited to, signals that a computer system hosting or running a computer program can be configured to access, including signals downloaded through the internet or other networks. Memory of the user device can be used to store and maintain any number of functional components that are executable by the one or more processors. In some implementations, these functional components include instructions or programs that are executable by the one or more processors of the user device and that, when executed, implement operational logic for performing the actions and services attributed above to user device.

Furthermore, memory of the user device can include one or more additional functional components, such as an operating system for controlling and managing various functions of the user device and for enabling basic user interactions.

In addition, the memory of the user device can also store data, data structures and the like, that are used by the functional components.

Memory of the user device can include one or more user interface module(s). User interface module(s) can be maintained in memory of the user device and executed on the processor(s) of the user device to perform acts. The acts can include one or more of receiving input regarding manufacturing data or administration data, receiving scanner data, associating manufacturing data or administration data with scanner data. Additionally or alternatively, the acts can include generating a user interface that allows a user to perform actions including one or more of view, sort, filter, or any combination thereof, information, input, data, etc. at varying levels of granularity. Additionally or alternatively, user interface module can cause a user interface to be provided to a user.

In an example, user interface module of the user device can be configured to provide a user interface that suits the particular user device being used by the user. For example, information can be presented to the user in a different manner when presented on a mobile phone than when presented on a personal computer. In an example, a user interface can be provided to a user via a web browser (e.g., software as a service (SaaS)), via a downloadable client application, or both.

Depending on the type of user device, the memory of the user device can also optionally include other functional components and data, such as other modules and data. Further, the user device can include many other logical, programmatic, and physical components, of which those described are merely examples that are related to the discussion herein.

I/O components of the user device can be configured to allow a user to interface with the user device via the one or more I/O devices. The I/O components of the user device can provide an interface for such devices as a display, speakers (not shown), a microphone (not shown), a keyboard (not shown), a mouse (not shown), a camera (not shown), an optical reader or scanner (not shown), a touchpad (not shown), a haptic output device (not shown) or any combination thereof.

In an example, the user device can include one or more displays. Depending on the type of computing device(s) used as user device, display can employ any suitable display technology. For example, display can be a liquid crystal display, a plasma display, a cathode ray tube (CRT) monitor, a light emitting diode display, an OLED (organic light-emitting diode) display, an electronic paper display, or any other suitable type of display able to present digital content thereon. In an example, the display(s) can have a touch sensor associated with display to provide a touchscreen display configured to receive touch inputs for enabling interaction with a graphic interface presented on display. Accordingly, implementations herein are not limited to any particular display technology. Alternatively, in an example, the user device may not include display, and information can be presented by other means, such as aurally.

One or more communication interface(s) can include one or more interfaces and hardware components for enabling communication with various other devices, such as over network(s) or directly. For example, the communication interface(s) can enable communication through one or more networks, which can include, but are not limited to any type of network known in the art such as a local area network or a wide area network, such as the Internet, and can include a wireless network, such as a cellular network, a local wireless network, such as Wi-Fi and/or close-range wireless communications, such as Bluetooth®, BLE, NFC, RFID, a wired network, or any other such network, or any combination thereof, etc. A network can include both wired and/or wireless communication technologies, including Bluetooth®, BLE, Wi-Fi and cellular communication technologies, as well as wired or fiber optic technologies, etc. Components used for such communications can depend at least in part upon the type of network, the environment selected, or both. Protocols for communicating over such networks are well known and will not be discussed herein in detail.

Other components included in the user device can include a GPS device (not shown) that is able to indicate location information. Further, the user device can include one or more sensors (not shown), such as an accelerometer, gyroscope, compass, proximity sensor, camera, microphone, and/or a switch, as discussed above. Additionally, the user device can include various other components that are not shown, examples of which include removable storage, a power source, such as a battery and power control unit, a printer, and so forth.

In an example, a third-party device (or, in embodiments, a device other than the user devices and the servers but associated with or managed by the same entity or organization) can operate intermediately between the server 502 and the user device(s) and/or scanning device(s). The third-party device can perform acts including but not limited to filtering formatting, anonymizing, pseudonymizing, analyzing of data, etc. In example, these acts depersonalize the data (e.g., remove the personally identifiable data). The third-party device can transmit the data to the server 502.

In embodiments, the third-party device can pseudonymize (alternatively spelled pseudonumise) at least some of the administration data. Pseudonymization takes personally identifiable information fields within a data record and replaces them with one or more artificial identifiers, or pseudonyms. In embodiments, one or more of the servers can pseudonymize administration data. In embodiments, the third-party device or server can additionally or alternatively encrypt the administration data. In embodiments, the third-party device or server can additionally or alternatively anonymize administration data.

Advances in medical care that can come from increased healthcare data access, such as those enabled by the present disclosure, are required to be counterbalanced by duties to protect personal data of patients. Techniques described herein allow for the removal of personally identifiable information from administration data. Techniques that anonymize data are traditionally irreversible and scrub personally identifiable information from the data permanently. However, anonymization techniques such as noise addition, differential privacy, permutation, aggregation/K-anonymity, and L-diversity/T-closeness can be used.

Some techniques, such as pseudonymization, allow personally identifiable information to be re-associated with the administration data if warranted for medical treatment or disease preventing. Other techniques that serve this purpose include using synthetic databases, quantum cryptography, secure multiparty computation, partial homomorphic encryption, and polymorphic encryption. By inserting an intervening third party device between the user device that transmits the administration data and the server that receives it, the privacy concerns of collection of such information can be alleviated. In embodiments, personally identifiable information may be removed by the user device or by the server.

In embodiments, administration data can be subject to qualified anonymity in which the data are pseudonymized for one entity (e.g., the treatment provider). That entity is the sole entity holding the re-identification key. However, for all third parties, the data is anonymized.

Pseudonymization and qualified anonymity allow the identifying of specific patients when those patients need to be informed of critical information (e.g., a vaccine was inactivated, contaminated, ineffective against a particular virus or strain, etc. so the patient is not immunized and may require another vaccination).

In embodiments, the present disclosure provides for obtaining patients' consent at the time of vaccination to allow identification of the patient from the collected data, if deemed necessary in the future.

In an embodiment, a third-party device can pseudonymize or encrypt those portions or data fields of the administration data that could specifically identify the patient by themselves or in combination with other data (e.g., name, date of birth, address, social security number or other government-issued identification number, medical record number).

In this way, the server receiving the administration data and associating it with the manufacturing data of the medicament would omit any personally identifiable information from reports and analyses it provides.

In an example, when an "outbreak" of a disease occurs, the server can provide information—without identifying any particular people—on which regions have been vaccinated with a certain medicament, the dates of vaccination of that medicament in the region, the percentage of the population in a region that has been vaccinated, etc. If, for example, there is a 95% immunization rate of persons in the region, the decision can be made that it unnecessary to send in a team to immunize that region. The team could be sent elsewhere where the immunization rate is lower. This results in conserved resources and more efficient medical responses.

In another example, if it is determined that a certain lot of medicament was inactivated, the third-party server (with permission of a health care provider or other authority, depending on applicable law, regulations, consent, etc.), can use the relevant subset of the administration data to query the identities of those who received the inactivated vaccine. Those people can then be contacted for follow up.

In another example, systems and methods described herein can help ensure that a medicament is manufactured and distributed in time for a second dose of the medicament. In an example, it can be determined using the techniques described herein that children in a village were vaccinated with a specific medicament on Jan. 1, 2019. Knowing that a follow up dose needs to be administered in one year for effective immunization, techniques described herein could be used to ensure that a sufficient amount of medicament was manufactured and distributed to the village by Jan. 1, 2020.

In embodiments, consent for access to the de-personalized data can be obtained at the time of vaccination. In an example, the patient (or parent or surrogate) signature can be associated with or included in the administration data. In examples, the patient can sign on a pressure-sensitive screen of the user device. In embodiments, a display of a user device used at or around the time of administration of the vaccine can include consent and treatment information (in the patient's own language and, in embodiments, provided aurally as well as displayed), and the patient, parent, or surrogate can sign at the indicated area of the display. An indication of the date and time can be associated with the signature and base transmitted as part of the administration data to the server (in embodiments, via a third-party device).

In examples, the patient can sign on paper, and the signature can be scanned or photographed and sent to the user device for association with the administration data.

In embodiments, information such as the administration data collected at the time of administration can be stored in association with the patient's health record with their local provider, in addition to be transmitted for association with the manufacturing data for the vaccine, using the same application or another application as is used to collect the administration data.

In embodiments, consent includes an acknowledgement that if there were a problem with the vaccine, i.e., inactivated, contaminated, ineffective against a particular virus or strain, that the individual's information could be accessed by the vaccine provider or healthcare provider (to the extent allowed by law) to follow-up or correct the problem.

Access to the personally identifiable information would be of benefit to the vaccine or medication recipient, in addition to the healthcare providers.

Figure 6:
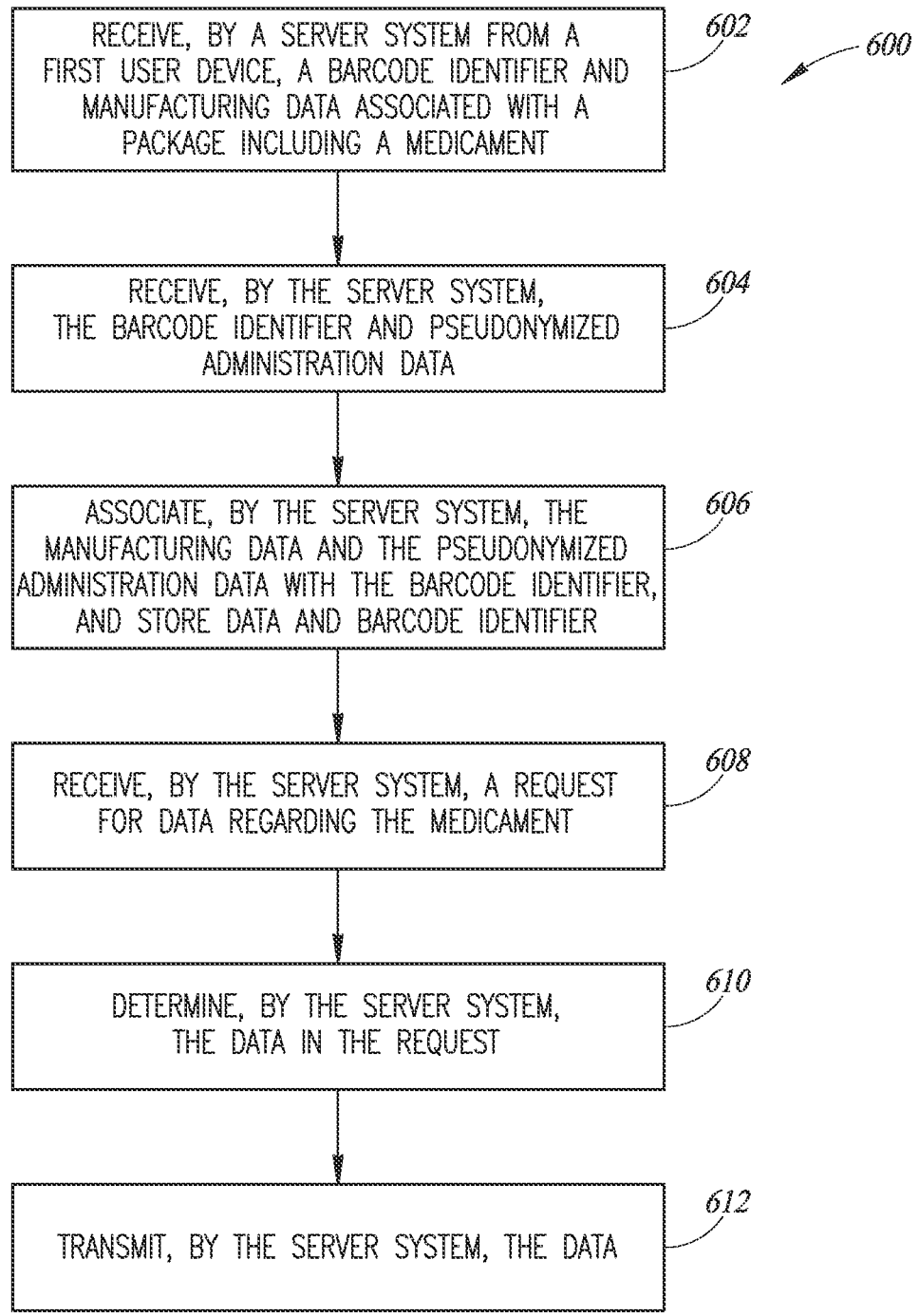
FIG. 6 illustrates a flow diagram of an example method for collecting and reporting on data associated with a barcode corresponding to a mixing/administration system.

FIG. 6 illustrates a flow diagram of an example method 600 for collecting and reporting on data associated with barcode(s) associated with mixing/administration systems.

At 602, a server system receives, from a first user device, manufacturing data associated with a packaging including a medicament and a barcode identifier associated with a barcode affixed to the packaging.

At 604, the server system receives pseudonymized administration data associated with administration of a vaccine that includes the medicament, and a barcode identifier associated with a barcode affixed to the packaging of the medicament. In examples, the administration data can be pseudonymized by a third-party device. In embodiments, a second user device transmits the administration data in association with the barcode identifier to a third-party device. In embodiments, the third-party device transmits the pseudonymized administration data to the server.

At 606, the server system associates the manufacturing data and the pseudonymized administration data with the barcode identifier (and to each other) and stores the manufacturing data, the pseudonymized administration data, the barcode identifier, and the association(s).

At 608, the server system receives a request for data regarding the medicament.

At 610, the server system determines, based at least in part on the manufacturing data and the administration data, the data in the request.

At 612, the server system transmits the data in the request.

Other data may be collected and associated with barcode(s) at the server system, and reports may include different types of information. In an example, the other data can be a location of the packaging while in transit to the place of administration.

An example method for making a system for tracking data can include first defining a data structure on a first type of device to store the collected data (e.g., medicament data, administration data, and patient data, wherein patient data can be a subset of administration data in embodiments). In embodiments, the data structure is configured to maintain privacy of the patient data while facilitating medicament or vaccine tracking by a managing entity.

The method further includes configuring a computer-readable medium associated with the first type of device to store the data structure, and configuring a processor associated with the first type of device to execute computer code to populate the medicament data portion of the data structure responsive to receiving, via a network interface associated with the first type of device, medicament data. The medicament data can include a barcode identifier.

In the example method, at least one of the administration data portion and/or the patient data portion of the data structure are populated with at least one of administration data and/or patient data, and wherein the administration data and/or patient data include a barcode identifier.

An application is programmed for execution on a second type of device. The application can provide a user interface, access input data for input of data, and then access a cryptographic processor associated with the second type of device to at least one of encrypt, anonymize, or pseudonymize at least part of at least one of input to generate depersonalized administration data. The depersonalized administration can be stored and at least part of the data can be provided upon request by a first user device, or other device.

EXAMPLE CLAUSES

Clause 1. A system comprising:
a syringe housing a medicament, wherein the medicament is in an amount effective for preventing, treating, or curing a particular disease;
a protective film encasing the syringe; and
a tracking mechanism for creating an association between data corresponding to manufacture of the medicament and data corresponding to administration of the medicament.

Clause 2. The system of clause 1, wherein the syringe comprises:
a syringe body comprising a cylindrical housing and a chamber within the cylindrical housing, the chamber having a longitudinal axis;
a piston comprising a stem having a first end and a second end opposing the first end, the first end being external to the chamber, the piston being insertable into the chamber and comprising a first opening at the first end and a second opening at the second end;
a fluid passageway from the first opening through the stem and through the second opening;
a third opening disposed at a position between the first end and the second end of the piston other than at the first or second end of the piston and traversing the fluid passageway;
a valve, at least a portion of which is inserted within the third opening and orthogonally traversing the fluid passageway, the valve controlling selective fluid passage through the piston and being at least partially insertable within the cylindrical housing of the syringe body;
a vial penetrator associated with the first end of the piston, the vial penetrator having a base having a first diameter, a head portion having a maximum width, and a tube segment extending between the base and the head portion, the tube segment having a second diameter that is smaller than the first diameter and shorter than the maximum width of the head portion;
a hollow extension extending from the first end of the piston; and
a piston seal attached to the second end of the piston.

Clause 3. A method comprising:
receiving, by one or more servers from a first instance of an application executing on a first user device, manufacturing data for a medicament, wherein the medicament is housed in a syringe and the syringe is encased in a protective film including a tracking mechanism, receiving, by the one or more servers from the first instance of the application executing on the first user device and in association with the manufacturing data, a tracking mechanism identifier corresponding to the tracking mechanism included on the protective film;
storing, by the one or more servers, the manufacturing data, the tracking mechanism identifier, and an association between the manufacturing data and the tracking mechanism identifier;
receiving, by the one or more servers, the tracking mechanism identifier and administration data, wherein the administration data comprises data corresponding to administration of the medicament to a recipient, wherein the administration data comprises a geolocation of the administration; and
based at least on identifying the existence of the association between the tracking mechanism identifier and the manufacturing data, storing, by the one or more servers, the administration data and an association between the administration data and the manufacturing data.

Clause 4. The method of clause 3, wherein the manufacturing data includes at least one of:
a chemical composition of the medicament;
an expiration date of the medicament;
a lot number for at least one of the medicament or a vial containing the medicament;
a manufacturer of at least one of the medicament or the vial;
a date of manufacture of at least one of the medicament or the vial;
a time of manufacture of at least one of the medicament or the vial; or
a location of manufacture of at least one of the medicament or the vial.

Clause 5. The method of clause 3 or 4, further comprising:
receiving, by the one or more servers, at least some of the manufacturing data and a request for the geolocation of the administration of the medicament; and
transmitting, by the one or more servers, and based at least in part the association between the administration data and the manufacturing data, the geolocation of the administration of the medicament Clause 6. The method of clause 3, 4, or 5, wherein the administration data further comprises at least one of:
a date of the administration of the medicament;
a time of the administration of the medicament;
an identifier of the recipient of the medicament, wherein the identifier can include one or more of a name, date of birth, and/or an identifying number;
a place of residence of recipient;
a geolocation of the administration;
demographic information of the recipient;
a name of a person performing the administration;
a dosage number; and/or
at least one vital sign of the recipient.

Clause 7. The method of any of clauses 3-6, wherein the syringe comprises the syringe device of clause 2.

Clause 8. The method of any of clauses 3-7, wherein the tracking mechanism comprises at least one of a linear barcode, a 2D barcode, a QR code, a datamatrix code, a PDF417 code, or a RFID tag.

Clause 9. The method of any of clauses 3-8, wherein the tracking mechanism comprises at least one of a linear barcode, a 2D barcode, a QR code, a datamatrix code, a PDF417 code, and wherein the tracking mechanism is printed on at least one of the protective film or a label affixed to the protective film.

Clause 10. The method of clause 9, wherein the tracking mechanism is additionally printed on at least one of the syringe or a label affixed to the syringe.

Clause 11. The method of any of clauses 3-10, wherein the tracking mechanism is included on a label affixed to the protective film, wherein the label further includes a viability indicator, wherein the viability indicator detects and indicates exposure of the label to a level of at least one of light or heat that could compromise viability of the medicament.

Clause 12. The method of any of clauses 3-8 or 11, wherein the tracking mechanism comprises a RFID tag, and wherein the RFID tag is affixed to the protective film.

Clause 13. The method of any of clauses 3-8 or 11-12, wherein the tracking mechanism comprises at least one RFID tag, and wherein a first RFID tag is included on the protective film and a second RFID tag is affixed to the syringe.

Clause 14. The method of any of clauses 3-13, further comprising:
receiving, by the one or more servers, additional administration data, wherein the additional administration data is associated with a plurality of recipients of the medicament; and
based at least on the additional administration data, generating a report indicating a target geolocation for remediation of defects of the medicament.

Clause 15. The method of any of clauses 3-14, further comprising:
receiving additional data associated with a plurality of recipients of the medicament; and
determining trends, based at least in part on the additional data, associated with the plurality of the recipients.

Clause 16. The method of any of clauses 3-15, wherein the request is regarding at least one of a plurality of syringes, a plurality of barcodes, or a plurality of medicaments.

Clause 17. The method of any of clauses 3-16, wherein receiving the tracking mechanism identifier and the administration data comprises receiving the tracking mechanism identifier and the administration data from a second instance of the application executing on a second user device.

Clause 18. The method of any of clauses 3-16, further comprising:
receiving, by a third-party device and from a second instance of the application executing on a second user device, the tracking mechanism identifier and the administration data; and
based at least on receiving the administration data, depersonalizing, by the intermediate computing device, the administration data via at least one of pseudonymization or anonymization,
wherein receiving, by the one or more servers, the administration data comprises receiving the depersonalized administration data from the third-party device.

Clause 19. The method of clause 18, further comprising:
receiving, by the one or more servers, a request for identification of one or more recipients of the medicament associated with the manufacturing data; and
transmitting, by the one or more servers to the intermediate computing device and based at least in part on the administration data, a request for an identity of the recipient;
providing, by the one or more servers from the intermediate computing device, the identity of the recipient.

Clause 20. The method of clause 17-19, wherein the second instance of the application executing on the second user device is configured to obtain the tracking mechanism identifier from a scanner associated with the second user device.

Clause 21. The method of clause 17-20, wherein the second instance of the application executing on the second user device is configured to obtain at least part of administration data from at least one of manual entry via a user interface of the application, from another application executing on the second user device, from a scanner associated with the second user device, or from a camera associated with the second user device.

Clause 22. One or more computer-readable media storing computer-executable instructions that, when executed by the one or more processors, cause the one or more processors to implement the method of any of clauses 3-21.

Clause 23. A system including one or more processors and one or more computer-readable media storing computer-executable instructions that, when executed by the one or more processors, implement the method of any of clauses 3-21.

Clause 24. A method comprising:
receiving, by one or more servers from a first instance of an application executing on a first user device, manufacturing data for a syringe encased in a protective film,
receiving, by the one or more servers from the first instance of the application executing on the first user device and in association with the manufacturing data, a tracking mechanism identifier corresponding to the tracking mechanism included on the protective film;
storing, by the one or more servers, the manufacturing data, the tracking mechanism identifier, and an association between the manufacturing data and the tracking mechanism identifier;
receiving, by the one or more servers from a second instance of the application executing on a second user device, the tracking mechanism identifier and administration data, wherein the administration data comprises data corresponding to administration of the medicament to a recipient, wherein the administration data comprises a geolocation of the administration; and
based at least on identifying the existence of the association between the tracking mechanism identifier and the manufacturing data, storing, by the one or more servers, the administration data and an association between the administration data and the manufacturing data.

Clause 25. The method of clause 24, wherein the manufacturing data includes at least one of:
a lot number for the syringe;
a manufacturer of the syringe;
a date of manufacture or packaging of the syringe;
a time of manufacture or packaging of the syringe;
a location of manufacture of the syringe;
components of the syringe; or
component manufacturing data.

Clause 26. The method of clause 24 or 25, further comprising:
receiving, by the one or more servers, at least some of the manufacturing data and a request for the geolocation of the administration of the medicament; and
transmitting, by the one or more servers, and based at least in part the association between the administration data and the manufacturing data, the geolocation of the administration of the medicament.

Clause 27. One or more computer-readable media storing computer-executable instructions that, when executed by the one or more processors, cause the one or more processors to implement the method of clauses 24-26.

Clause 28. A system including one or more processors and one or more computer-readable media storing computer-executable instructions that, when executed by the one or more processors, implement the method of clauses 24-26.

Clause 29. A method of making a tracking system comprising:

defining a data structure for storage of medicament data, administration data, and patient data on at least one first type of device, wherein the data structure includes at least a medicament data portion, an administration data portion, and a patient data portion, and the data structure is configured to maintain privacy of the patient data while facilitating medicament or vaccine tracking by a managing entity;

configuring a computer-readable medium associated with the first type of device to store the data structure;

configuring a processor associated with the first type of device to execute computer code to populate:

the medicament data portion of the data structure responsive to receiving, via a network interface associated with the first type of device, medicament data, wherein the medicament data includes a barcode identifier;

at least one of the administration data portion and/or the patient data portion of the data structure responsive to receiving via the network interface associated with the first type of device, transmitted data, wherein the transmitted data includes at least one of administration data and/or patient data, and wherein the administration data and/or patient data include a barcode identifier;

programming an application for execution on a second type of device, the application configured to:

provide a graphical user interface for presentation on a screen associated with the second type of device;

access one or more input devices associated with the second type of device, wherein the input device comprises at least one of:

a camera or other scanning device associated with the second type of device to receive image input of one or more images;

a keyboard input device associated with the second type of device, the keyboard input device to receive keyboard input:

a microphone associated with the second type of device to receive audio input;

receive at least one of image input, keyboard input, or audio input;

receive log-in credentials of a user of the second type of device via one or more of the camera, the keyboard input device, and/or the microphone;

access a storage device associated with the second type of device to store input received associated with the application; and access a network interface associated with the second type of device to send toward the first type of device at least a part of the input received associated with the application as transmitted data.

Clause 30. The method of clause 29, the application further configured to:

access a cryptographic processor associated with the second type of device to at least one of encrypt, anonymize, or pseudonymize at least part of at least one of the image input, the keyboard input, or the audio input to generate depersonalized administration data;

Clause 31. The method of clause 29 or 30, wherein the medicament data comprises at least one of:

a date of manufacture of at least one of the medicament or a vial housing the medicament;

a time of manufacture of at least one of the medicament or the vial;

a location of manufacture of at least one of the medicament or the vial;

packaging information of at least one of the medicament or the vial;

shipping information of at least one of the medicament or the vial;

dosage information of the medicament;

a chemical composition of the medicament;

an expiration date of the medicament;

a lot number for at least one of the medicament or the vial;

a manufacturer of at least one of the medicament or the vial;

Clause 32. The method of clause 29, 30, or 31, wherein the one or more images include one or more of:

an image of a barcode;

an image of a treatment provider;

an image of identification of the treatment provider; and/or an image of a patient and/or an image of identification of the patient.

Clause 33. The method of any of clauses 29-32, wherein the keyboard input device includes at least one of a hardware keyboard and/or a soft keyboard on the screen associated with the second type of device, and wherein the keyboard input includes at least one of:

a name associated with a treatment provider;

an identification number associated with the treatment provider;

a name associated with the patient; and/or an identification number associated with the patient.

Clause 34. The method of any of clauses 29-33, wherein the audio input includes at least one of:

numerals associated with a barcode;

a name associated with the treatment provider;

an identification number associated with the treatment provider;

a name associated with the patient; and/or an identification number associated with the patient.

Clause 35. One or more computer-readable media storing computer-executable instructions that, when executed by the one or more processors, cause the one or more processors to implement the method of any of clauses 29-34.

Clause 36. A system including one or more processors and one or more computer-readable media storing computer-executable instructions that, when executed by the one or more processors, implement the method of any of clauses 29-34.

Clause 37. A device comprising:

a syringe body comprising a cylindrical housing and a chamber within the housing, the chamber having a longitudinal axis;

a piston comprising a stem having a first end and a second end opposing the first end, the first end being external to the chamber, the piston being insertable into the chamber and comprising a first opening at the first end and a second opening at the second end;

a fluid passageway extending from the first opening through the second opening;

a third opening disposed at a position between the first end and the second end of the piston other than at the first or second end of the piston and traversing the fluid passageway;

a valve, at least a portion of which is inserted within the third opening and orthogonally traversing the fluid passageway, the valve controlling selective fluid passage through the piston and being at least partially insertable within the cylindrical housing of the syringe body;

a vial penetrator associated with the first end of the piston, the vial penetrator having a base having a first diameter, a head portion having a maximum width, and a tube segment extending between the base and the head portion, the tube segment having a second diameter that is smaller than the first diameter and shorter than the maximum width of the head portion;

a hollow extension extending from the first end of the piston;

a piston seal attached to the second end of the piston; and two or more caps, wherein at least one of the two or more caps is detachably attached to an end of the syringe body that is closer to the second end of the piston, and wherein at least one of the two or more caps includes a composition comprising at least one of a cleansing, antiseptic, antimicrobial, disinfectant. or hemostatic agent.

Clause 38. The device of clause 37, wherein a first cap of the two or more caps is detachably coupled to a second cap of the two or more caps.

Clause 39. The device of clause 37 or 38, wherein at least one of the two or more caps comprises:

a cavity;

an outer surface configured to interface with a user;

an inner surface within the cavity; and a foam applicator material attached to the inner surface within the cavity containing the composition comprising:

from about 1 mg/mL to about 50 mg/mL of ethylenediaminetetraacetic acid (EDTA), acids of EDTA, salts of EDTA, citrate, salts of citrate or any combination thereof;

from about 20% to about 70% ethanol, by volume;

from about 0.5% to about 7.5% hydrogen peroxide, by volume; and water.

Clause 40. The device of clause 39, wherein the foam applicator material comprises a shape substantially similar to a shape of each cavity of the at least one cap.

Clause 41. The device of clause 39 or 40, wherein the foam applicator material of at least one cap is maintained in a compressed state while the at least one cap is sealed and the foam applicator material of the at least one cap is configured to extend outside the cavity of the at least one cap when the at least one cap is unsealed.

Clause 42. The device of clause 39, 40, or 41, wherein the foam applicator material comprises a permeable material with different surface treatments, finishes, contours, or combinations thereof.

Clause 43. The device of clause 39, 40, 41, or 42, wherein the foam applicator material comprises at least one of starch polymer, cellulosic gel, polyurethane, silicone, silicone rubber, polyethylene, polypropylene, thermoplastic elastomer, or mixtures thereof.

Clause 44. The device of any of clauses 37-43, wherein at least one of the two or more caps is operable to cause hemostasis at an injection site.

Clause 45. The device of clause 44, wherein the at least one cap causes hemostasis at least in part by providing a surface to press against a site of bleeding.

Clause 46. The device of clause 44, wherein the at least one cap includes at least one of an antihemorrhagic agent or a procoagulant agent that, when applied to a site of bleeding, causes hemostasis.

Clause 47. The device of any of clauses 37-46, wherein a second cap of the two or more caps is stored within a cavity of a first cap of the two or more caps.

Clause 48. The device of clause 47, wherein the second cap includes a removable protective lid and a second composition comprising at least one of a cleansing, antiseptic, antimicrobial, or disinfectant agent, wherein the second composition is at least one of a liquid or a gel.

Clause 49. The device of clause 47, wherein the second cap is operable to cause hemostasis at an injection site.

Clause 50. The device of clause 47, wherein at least one of the first cap and the second cap comprise at least one of polypropylene, polyethylene, copolymer material, or mixtures thereof.

Clause 51. The device of clause 38, wherein the first cap and the second cap are coupled by a heat seal.

Clause 52. The device of clause 39-43, wherein the foam applicator material of a first cap contains a composition different from a composition contained by the foam applicator of a second cap.

Clause 53. The device of clause 37 or 38, wherein detaching the first cap from the second cap comprises at least one of twisting, pulling, snapping, or bending the first cap away from the second cap.

Clause 54. The device of any of clauses 37-53, further comprising:

a protective film encasing the syringe device; and a tracking mechanism.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

One skilled in the art will realize that a virtually unlimited number of variations to the above descriptions are possible, and that the examples and the accompanying figures are merely to illustrate one or more embodiments or examples of implementations.

It will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular embodiments disclosed, but that such claimed subject matter may also include all embodiments falling within the scope of the appended claims, and equivalents thereof.

In the detailed description above, numerous specific details are set forth to provide a thorough understanding of claimed subject matter. However, it will be understood by those skilled in the art that claimed subject matter may be practiced without these specific details. In other instances, methods, apparatuses, or systems that would be known by one of ordinary skill have not been described in detail so as not to obscure claimed subject matter.

Reference throughout this specification to "one embodiment" or "an embodiment" may mean that a particular feature, structure, or characteristic described in connection with a particular embodiment may be included in at least one embodiment of claimed subject matter. Thus, appearances of the phrase "in one embodiment" or "an embodiment" in various places throughout this specification are not necessarily intended to refer to the same embodiment or to any one particular embodiment described. Furthermore, it is to be understood that particular features, structures, or characteristics described may be combined in various ways in one or more embodiments. In general, of course, these and other issues may vary with the particular context of usage. Therefore, the particular context of the description or the usage of these terms may provide helpful guidance regarding inferences to be drawn for that context.

Conditional language such as, among others, "can," "could," "might" or "may," unless specifically stated otherwise, are understood within the context to present that certain examples or embodiments include, while other examples or embodiments do not include, certain features, elements and/or steps. Thus, such conditional language is not generally intended to imply that certain features, elements and/or steps are in any way required for one or more examples or embodiments or that one or more examples or embodiments necessarily include logic for deciding, with or without user input or prompting, whether certain features, elements and/or steps are included or are to be performed in any particular example or embodiment. Conjunctive language such as the phrase "at least one of X, Y or Z," unless specifically stated otherwise, is to be understood to present that an item, term, etc., can be either X, Y, or Z, or a combination thereof.

What is claimed is:

1. A method comprising:
   receiving, by one or more servers from a first instance of an application executing on a first user device, manufacturing data for a medicament, wherein the medicament is housed in a syringe and the syringe is encased in a protective film including a tracking mechanism,
   receiving, by the one or more servers from the first instance of the application executing on the first user device and in association with the manufacturing data, a tracking mechanism identifier corresponding to the tracking mechanism included on the protective film;
   storing, by the one or more servers, the manufacturing data, the tracking mechanism identifier, and an association between the manufacturing data and the tracking mechanism identifier;
   receiving, by the one or more servers, the tracking mechanism identifier and administration data, wherein the administration data comprises data corresponding to administration of the medicament to a recipient, wherein the administration data comprises a geolocation of the administration; and
   based at least on identifying the existence of the association between the tracking mechanism identifier and the manufacturing data, storing, by the one or more servers, the administration data and an association between the administration data and the manufacturing data.

2. The method of claim 1, wherein the manufacturing data includes at least one of:
   a chemical composition of the medicament;
   an expiration date of the medicament;
   a lot number for at least one of the medicament or a vial containing the medicament;
   a manufacturer of at least one of the medicament or the vial;
   a date of manufacture of at least one of the medicament or the vial;
   a time of manufacture of at least one of the medicament or the vial; or
   a location of manufacture of at least one of the medicament or the vial.

3. The method of claim 1, further comprising:
   receiving, by the one or more servers, at least some of the manufacturing data and a request for the geolocation of the administration of the medicament; and
   transmitting, by the one or more servers, and based at least in part the association between the administration data and the manufacturing data, the geolocation of the administration of the medicament.

4. The method of claim 1, wherein the administration data further comprises at least one of:
   a date of the administration of the medicament;
   a time of the administration of the medicament;
   an identifier of the recipient of the medicament, wherein the identifier can include one or more of a name, date of birth, and/or an identifying number;
   a place of residence of recipient;
   a geolocation of the administration;
   demographic information of the recipient;
   a name of a person performing the administration;
   a dosage number; and/or
   at least one vital sign of the recipient.

5. The method of claim 1, wherein the tracking mechanism comprises at least one of a linear barcode, a 2D barcode, a QR code, a datamatrix code, a PDF417 code, or a RFID tag.

6. The method of claim 1, wherein the tracking mechanism comprises at least one of a linear barcode, a 2D barcode, a QR code, a datamatrix code, a PDF417 code, and wherein the tracking mechanism is printed on at least one of the protective film or a label affixed to the protective film.

7. The method of claim 6, wherein the tracking mechanism is additionally printed on at least one of the syringe or a label affixed to the syringe.

8. The method of claim 1, wherein the tracking mechanism is included on a label affixed to the protective film, wherein the label further includes a viability indicator, wherein the viability indicator detects and indicates exposure of the label to a level of at least one of light or heat that could compromise viability of the medicament.

9. The method of claim 1, wherein the tracking mechanism comprises a RFID tag, and wherein the RFID tag is affixed to the protective film.

10. The method of claim 1, wherein the tracking mechanism comprises at least one RFID tag, and wherein a first RFID tag is included on the protective film and a second RFID tag is affixed to the syringe.

11. The method of claim 1, further comprising:
    receiving, by the one or more servers, additional administration data, wherein the additional administration data is associated with a plurality of recipients of the medicament; and
    based at least on the additional administration data, generating a report indicating a target geolocation for remediation of defects of the medicament.

12. The method of claim 1, further comprising:
    receiving additional data associated with a plurality of recipients of the medicament; and
    determining trends, based at least in part on the additional data, associated with the plurality of the recipients.

13. The method of claim 1, wherein the request is regarding at least one of a plurality of syringes, a plurality of barcodes, or a plurality of medicaments.

14. The method of claim 1, wherein receiving the tracking mechanism identifier and the administration data comprises receiving the tracking mechanism identifier and the administration data from a second instance of the application executing on a second user device.

15. The method of claim 1, further comprising:
receiving, by a third-party device and from a second instance of the application executing on a second user device, the tracking mechanism identifier and the administration data; and
based at least on receiving the administration data, depersonalizing, by the intermediate computing device, the administration data via at least one of pseudonymization or anonymization,
wherein receiving, by the one or more servers, the administration data comprises receiving the depersonalized administration data from the third-party device.

16. The method of claim 15, further comprising:
receiving, by the one or more servers, a request for identification of one or more recipients of the medicament associated with the manufacturing data; and
transmitting, by the one or more servers to the intermediate computing device and based at least in part on the administration data, a request for an identity of the recipient;
providing, by the one or more servers from the intermediate computing device, the identity of the recipient.

17. The method of claim 15, wherein the second instance of the application executing on the second user device is configured to obtain the tracking mechanism identifier from a scanner associated with the second user device.

18. The method of claim 15, wherein the second instance of the application executing on the second user device is configured to obtain at least part of administration data from at least one of manual entry via a user interface of the application, from another application executing on the second user device, from a scanner associated with the second user device, or from a camera associated with the second user device.

* * * * *